United States Patent
Choi et al.

(10) Patent No.: US 8,420,231 B2
(45) Date of Patent: Apr. 16, 2013

(54) IRIDIUM PHOSPHORESCENT DENDRIMER, METHOD OF PREPARING THE SAME AND ELECTROLUMINESCENT DEVICE INCLUDING THE IRIDIUM PHOSPHORESCENT DENDRIMER

(75) Inventors: Dong-hoon Choi, Seoul (KR); Kyung-moon Jung, Jeollanam-do (KR); Min-ju Cho, Suwon-si (KR)

(73) Assignees: Samsung Electronics Co., Ltd. (KR); SNU R&DB Foundation (KR)

( * ) Notice: Subject to any disclaimer, the term of this patent is extended or adjusted under 35 U.S.C. 154(b) by 546 days.

(21) Appl. No.: 12/576,115

(22) Filed: Oct. 8, 2009

(65) Prior Publication Data
US 2010/0084970 A1 Apr. 8, 2010

(30) Foreign Application Priority Data

Oct. 8, 2008 (KR) .......................... 10-2008-0098876
Sep. 22, 2009 (KR) .......................... 10-2009-0089651

(51) Int. Cl.
*H01L 51/54* (2006.01)
*C09K 11/06* (2006.01)

(52) U.S. Cl.
USPC ........... 428/690; 428/917; 313/504; 313/506; 252/301.16; 257/40; 257/102; 257/E51.044; 548/103

(58) Field of Classification Search .................. None
See application file for complete search history.

(56) References Cited

U.S. PATENT DOCUMENTS

2006/0237715 A1* 10/2006 Park et al. ...................... 257/40
2006/0280964 A1* 12/2006 Liu ............................... 428/690

OTHER PUBLICATIONS

Jung et al. "Deep-red light-emitting phosphorescent dendrimer encapsulated tris[2-benzo[b]thiophen-2-yl-pyridyl]iridium(III) core for light-emitting device applications." Journal of Polymer Science: Part A. vol. 46, pp. 7517-7533. 2008.*

Anthopoulos, T. D. et al., Solution-Processable Red Phosphorescent Dendrimers for Light-Emitting Device Applications, Adv. Mater., 2004, vol. 16 (6): pp. 557-560.

Li, B.L. et al., The synthesis and properties of Iridium(III)-cored dendrimers with carbazole peripherally functionalized-beta-diketonato dendrons, Dalton Trans. 2007 (20): pp. 2048-2057; E-pub May 9, 2007.

Lo, S.C. et al., A Light-Blue Phosphorescent Dendrimer for Efficient Solution-Processed Light-Emitting Diodes, Adv. Funct. Mater., 2005, vol. 15 (9): pp. 1451-1458.

Zhou, G. et al., Triphenylamine-Dendronized Pure Red Iridium Phosphors with Superior OLED Efficiency/Color Purity Trade-Offs, Angew. Chem. Int. Ed. 2007, vol. 46; pp. 1149-1151.

* cited by examiner

*Primary Examiner* — Michael H Wilson
(74) *Attorney, Agent, or Firm* — Cantor Colburn LLP

(57) ABSTRACT

An iridium phosphorescent dendrimer represented by Formula 1:

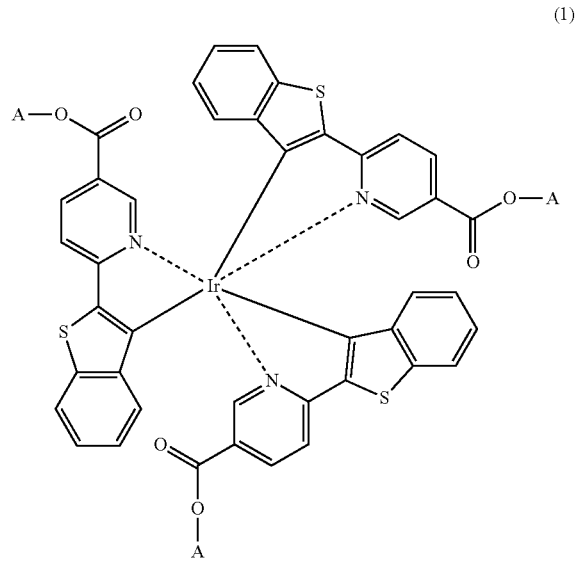

(1)

wherein A is a carbazole-based dendron. Also disclosed is a method of preparing the iridium phosphorescent dendrimer and an electroluminescent device including the iridium phosphorescent dendrimer.

9 Claims, 18 Drawing Sheets

IRIDIUM PHOSPHORESCENT DENDRIMER, METHOD OF PREPARING THE SAME AND ELECTROLUMINESCENT DEVICE INCLUDING THE IRIDIUM PHOSPHORESCENT DENDRIMER

CROSS-REFERENCE TO RELATED APPLICATIONS

This application claims priority to Korean Patent Application No. 10-2008-0098876, filed on Oct. 8, 2008, and Korean Patent Application No. 10-2009-0089651, filed on Sep. 22, 2009, and all the benefits accruing therefrom under 35 U.S.C. §119, the contents of which in their entirety are herein incorporated by reference.

BACKGROUND

1. Field

This disclosure relates to an iridium phosphorescent dendrimer, a method of preparing the iridium phosphorescent dendrimer and an electroluminescent device including the iridium phosphorescent dendrimer, and more particularly, to an iridium phosphorescent dendrimer exhibiting good self-film forming properties, a method of preparing the iridium phosphorescent dendrimer exhibiting good self-film forming properties and an electroluminescent device including the iridium phosphorescent dendrimer exhibiting good self-film forming properties.

2. Description of the Related Art

Semiconducting organic materials have attracted considerable interest as candidate materials for electronic and optoelectronic devices. Electroluminescent ("EL") devices using semiconducting organic materials have gained popularity and are already being used in practical applications such as flat-panel displays and flexible display devices.

In particular, dendrimer light-emitting materials (DLED) may be used to provide fast response, high brightness, low driving voltage, ease of device fabrication, and good processability Cyclometalated Ir(III) complexes including DLED show high phosphorescent efficiency.

Organic light-emitting diodes ("OLEDs") including cyclometalated Ir(III) complexes are fabricated by repeated thermal evaporation to provide several organic layers. However, the thermal vacuum deposition process for fabricating EL devices is relatively complicated and costly. Also, doping an iridium complex into a host polymer or large molecule is disadvantageous due to phosphorescent self-quenching, phase separation and insufficient energy transfer, thereby leading to fast decay of luminescence efficiency and external quantum efficiency ("EQE") with an increase in current density. Thus, there is a need for an iridium phosphorescent dendrimer that may be used without a host and that can form an organic layer by a solution process.

SUMMARY

One or more embodiments include an iridium phosphorescent dendrimer exhibiting good self-film forming properties, and a method of preparing the iridium phosphorescent dendrimer.

One or more embodiments include an electroluminescent device including the iridium phosphorescent dendrimer.

Additional aspects will be set forth in part in the description which follows and, in part, will be apparent from the description, or may be learned by practice of the presented embodiments.

According to one or more embodiments, there is provided an iridium phosphorescent dendrimer represented by Formula 1:

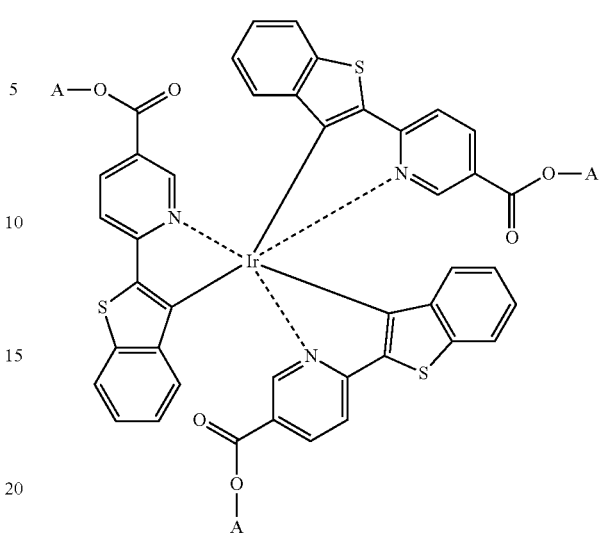

wherein A is a carbazole-based dendron.

In an embodiment, A may be represented by any one of Formulas 2, 3 and 4:

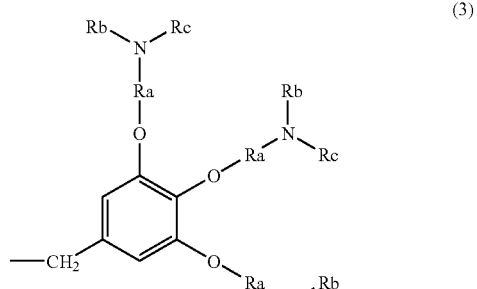

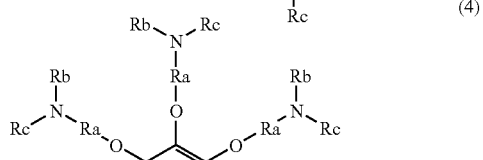

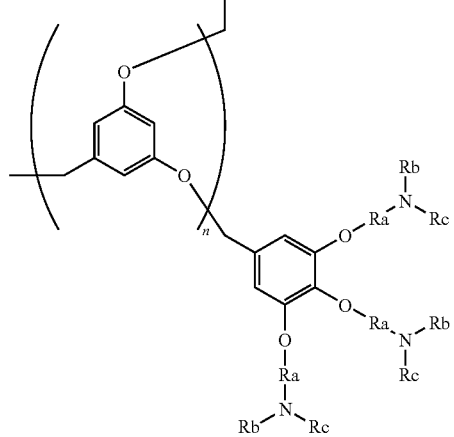

wherein Ra is a $C_1$-$C_{22}$ alkylene group, a $C_2$-$C_{22}$ alkenylene group, a $C_5$-$C_{30}$ arylene group or a $C_6$-$C_{30}$ aminoarylene group, wherein the alkylene group, the arylene group or the aminoarylene group each optionally includes at least one heteroatom selected from the group consisting of Si, B, O, P, N and S, wherein Rb and Rc are each independently a $C_1$-$C_{22}$ alkylene group, a $C_5$-$C_{30}$ arylene group or a $C_6$-$C_{30}$ aminoarylene group, wherein the alkylene group, the arylene group or the aminoaryl group optionally includes at least one heteroatom selected from the group consisting of Si, B, O, P, N and S, wherein Rb and Rc are connected via a single bond, an alkylene group, or an alkenylene group so as to form a fused ring, n is an integer from 1 through 5, and wherein the iridium phosphorescent dendrimer is homoleptic.

According to one or more embodiments, there is provided a method of preparing an iridium phosphorescent dendrimer represented by Formula 1:

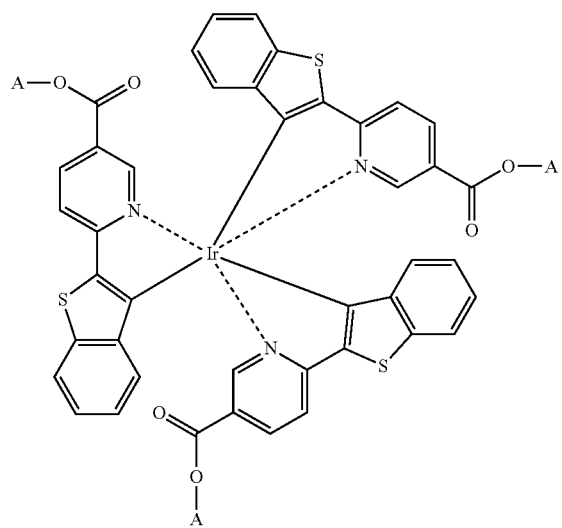

(1)

the method including contacting the tris-(2-benzo[b]thiophen-2-yl-nicotinic acid) Iridium (III) complex of Formula 5:

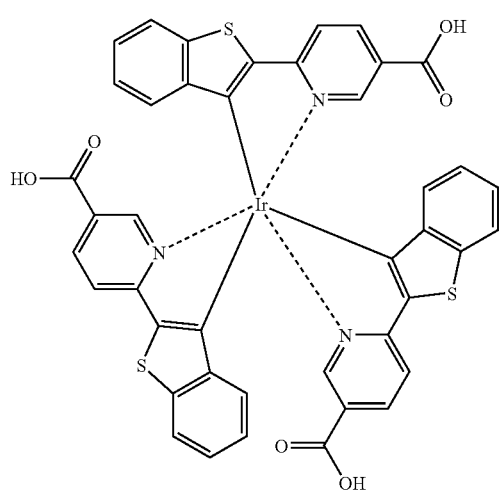

(5)

with carbazolyl alcohol, wherein A is a carbazole-based dendron.

According to one or more embodiments there is provided an electroluminescent device including the iridium phosphorescent dendrimer of Formula 1:

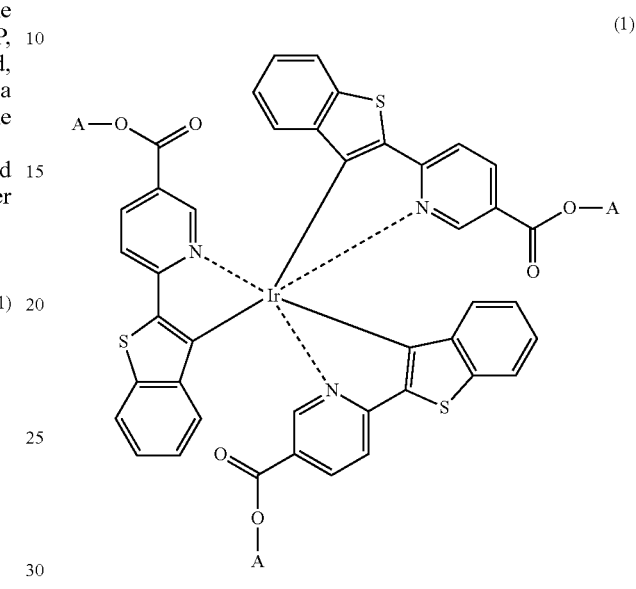

(1)

wherein A is a carbazole-based dendron.

BRIEF DESCRIPTION OF THE DRAWINGS

These and/or other aspects, features and advantages of this disclosure will become apparent and more readily appreciated from the following description of the embodiments, taken in conjunction with the accompanying drawings in which.

DETAILED DESCRIPTION

Figure 1A:
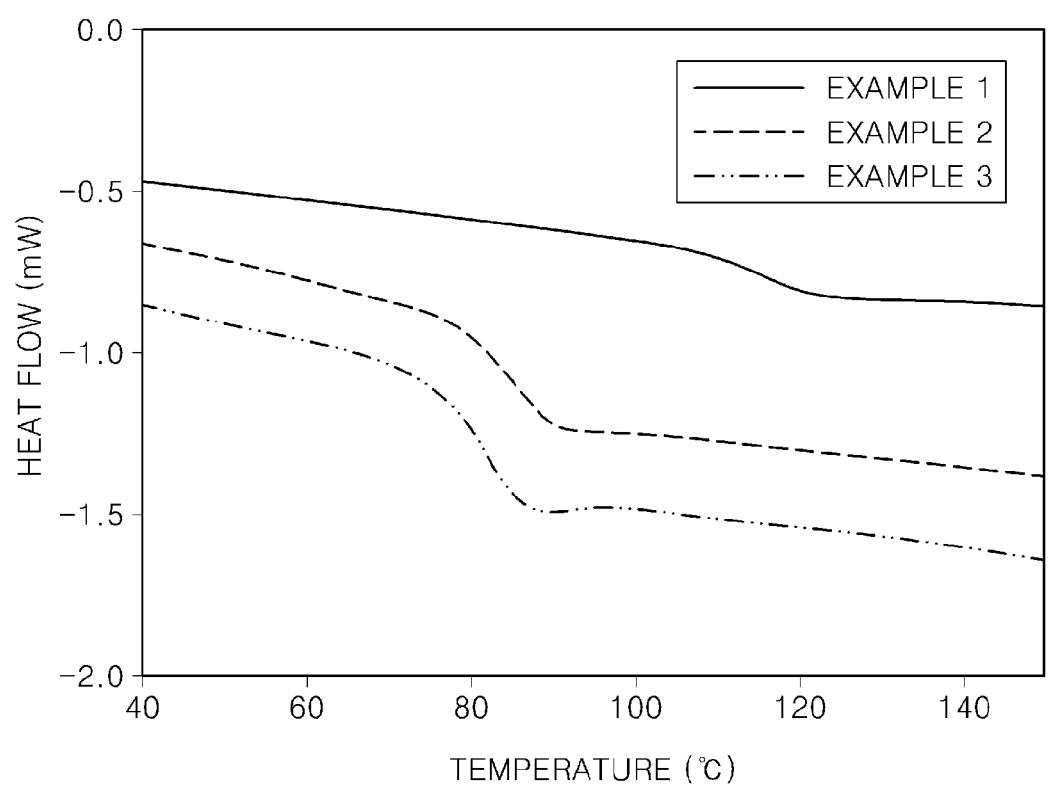
FIG. 1A is a differential scanning calorimetry ("DSC") thermogram illustrating heat flow (milliwatts) versus temperature (degrees Celsius, (° C.)) of phosphorescent dendrimers prepared according to Examples 1 to 3 and analyzed according to Example 4.

The invention now will be described more fully hereinafter with reference to the accompanying drawings, in which various embodiments are shown. This invention may, however, be embodied in many different forms, and should not be construed as limited to the embodiments set forth herein. Rather, these embodiments are provided so that this disclosure will be thorough and complete, and will fully convey the scope of the invention to those skilled in the art. Like reference numerals refer to like elements throughout.

It will be understood that when an element is referred to as being "on" another element, it can be directly on the other element or intervening elements may be present therebetween. In contrast, when an element is referred to as being "directly on" another element, there are no intervening elements present. As used herein, the term "and/or" includes any and all combinations of one or more of the associated listed items.

It will be understood that, although the terms first, second, third etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, a first element, component, region, layer or section discussed below could be termed a second element, component, region, layer or section without departing from the teachings of the present invention.

The terminology used herein is for the purpose of describing particular embodiments only and is not intended to be limiting. As used herein, the singular forms "a," "an" and "the" are intended to include the plural forms as well, unless the context clearly indicates otherwise. It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Furthermore, relative terms, such as "lower" or "bottom" and "upper" or "top," may be used herein to describe one element's relationship to another elements as illustrated in the Figures. It will be understood that relative terms are intended to encompass different orientations of the device in addition to the orientation depicted in the Figures. For example, if the device in one of the figures is turned over, elements described as being on the "lower" side of other elements would then be oriented on "upper" sides of the other elements. The exemplary term "lower," can therefore, encompasses both an orientation of "lower" and "upper," depending on the particular orientation of the figure. Similarly, if the device in one of the figures is turned over, elements described as "below" or "beneath" other elements would then be oriented "above" the other elements. The exemplary terms "below" or "beneath" can, therefore, encompass both an orientation of above and below.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Exemplary embodiments are described herein with reference to cross section illustrations that are schematic illustrations of idealized embodiments. As such, variations from the shapes of the illustrations as a result, for example, of manufacturing techniques and/or tolerances, are to be expected. Thus, embodiments described herein should not be construed as limited to the particular shapes of regions as illustrated herein but are to include deviations in shapes that result, for example, from manufacturing. For example, a region illustrated or described as flat may, typically, have rough and/or nonlinear features. Moreover, sharp angles that are illustrated may be rounded. Thus, the regions illustrated in the figures are schematic in nature and their shapes are not intended to illustrate the precise shape of a region and are not intended to limit the scope of the present claims.

Hereinafter, a phosphorescent dendrimer, a method of preparing the phosphorescent dendrimer and an electroluminescent device including the phosphorescent dendrimer will be further described with reference to exemplary embodiments.

In an embodiment, an iridium phosphorescent dendrimer may be represented by Formula 1:

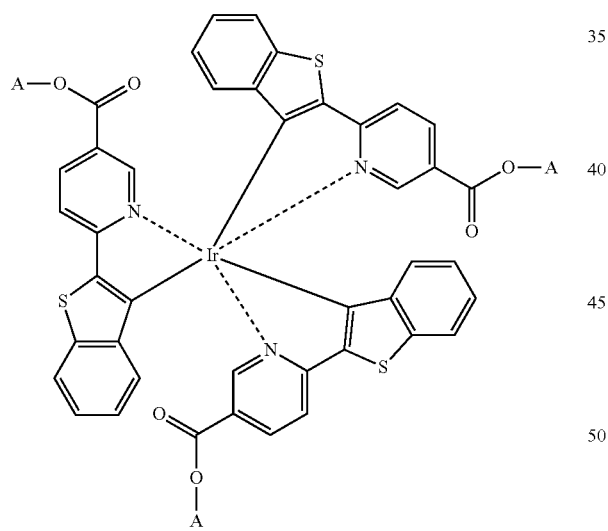

(1)

wherein A is a carbazole-based dendron.

In Formula 1, A may be represented by any one of Formulas 2, 3 and 4:

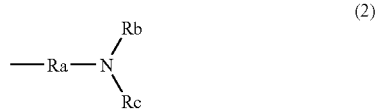

(2)

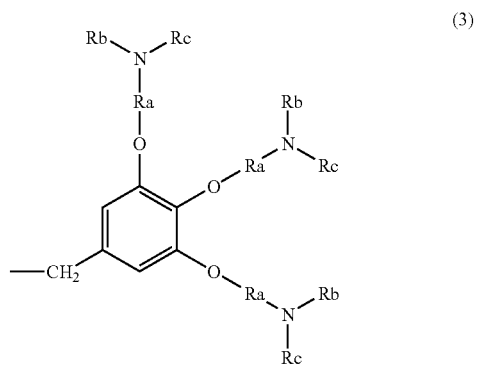

(3)

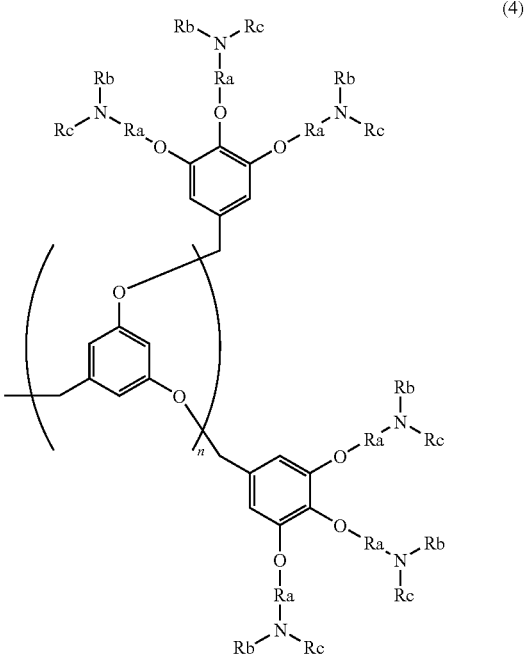

(4)

wherein Ra is a $C_1$-$C_{22}$ alkylene group, a $C_2$-$C_{22}$ alkenylene group, a $C_5$-$C_{30}$ arylene group or a $C_6$-$C_{30}$ aminoarylene group, wherein the alkylene group, the arylene group or the aminoarylene group optionally each includes at least one heteroatom selected from the group consisting of Si, B, O, P, N and S; wherein Rb and Rc are each independently a $C_1$-$C_{22}$ alkyl group, a $C_5$-$C_{30}$ aryl group or a $C_6$-$C_{30}$ aminoaryl group, wherein the alkyl group, the aryl group or the aminoaryl group each optionally includes at least one heteroatom selected from the group consisting of Si, B, O, P, N and S, wherein Rb and Rc are connected via a single bond, an alkylene group or an alkenylene group so as to form a fused ring, and wherein n is an integer from 1 through 5.

In an embodiment, the iridium phosphorescent dendrimer is represented by any one of Formulas 6, 7 and 8:

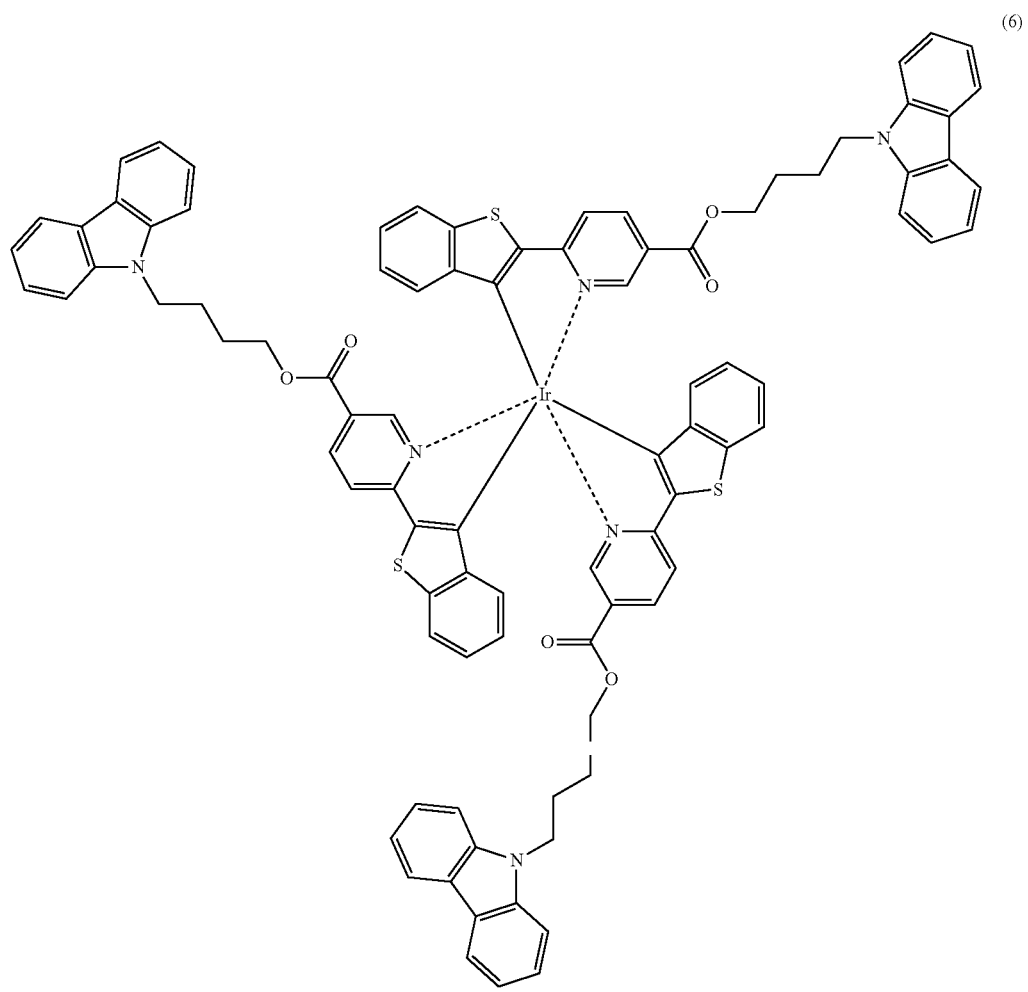
(6)

(7)
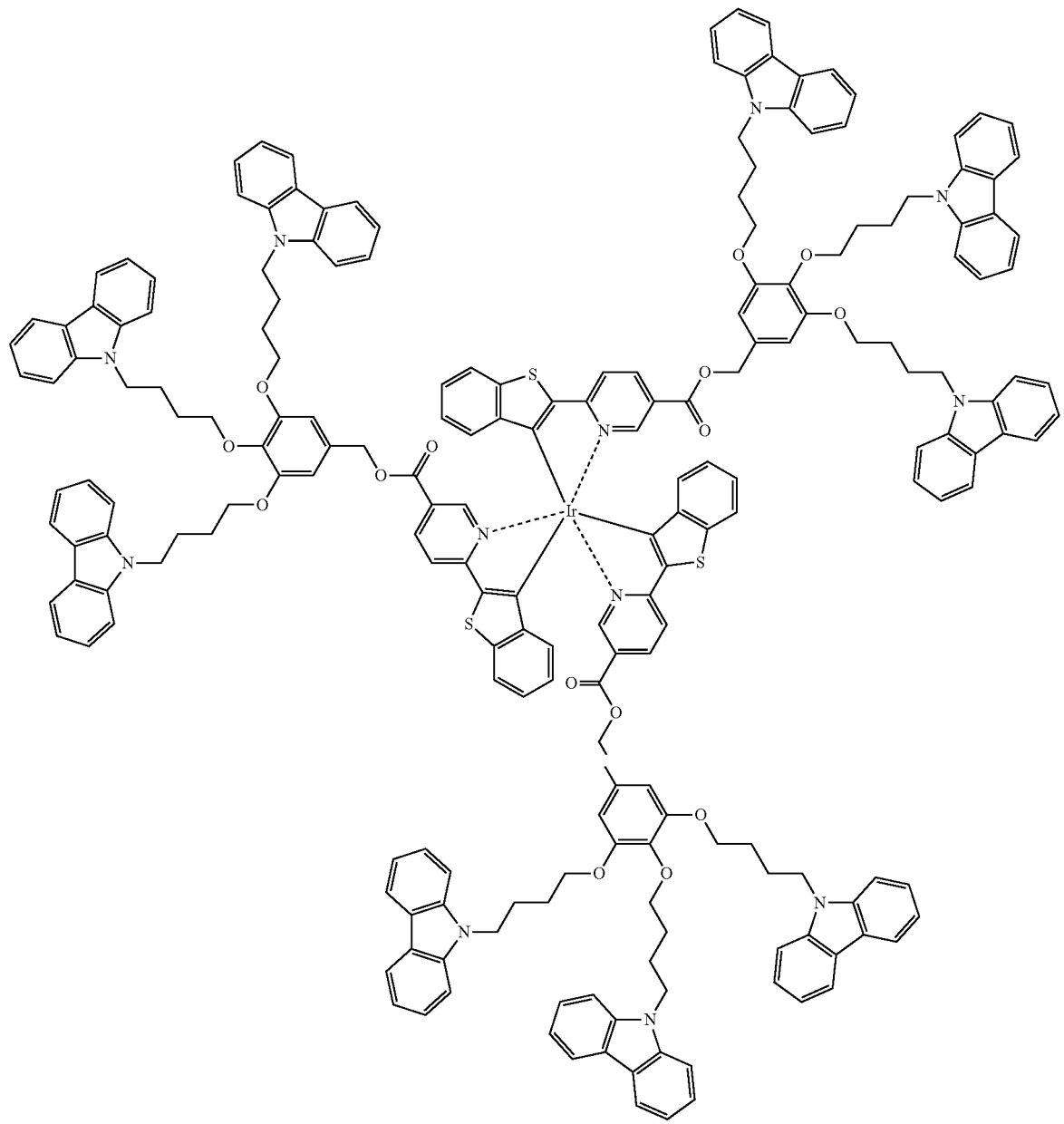

-continued
(8)
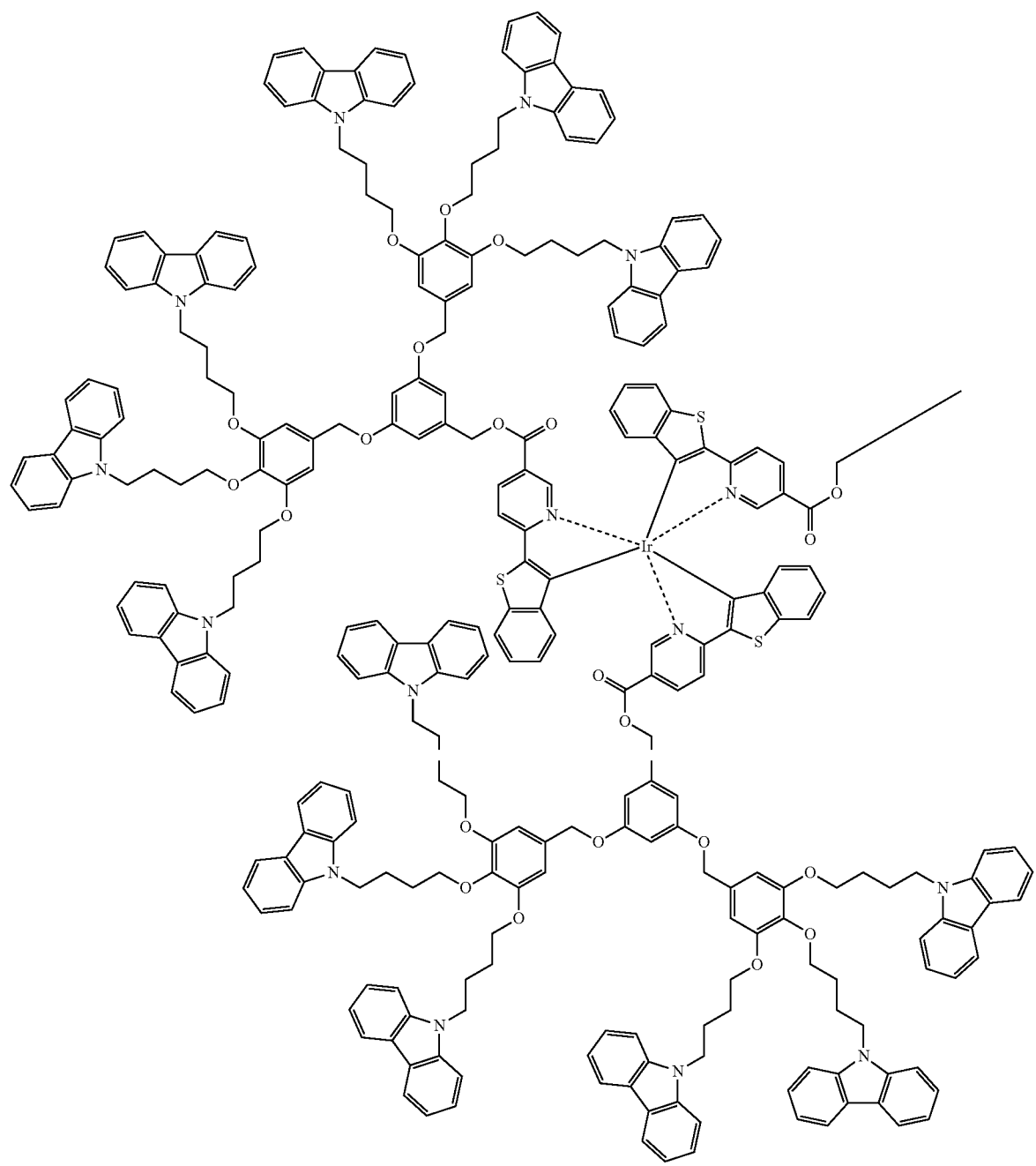

-continued

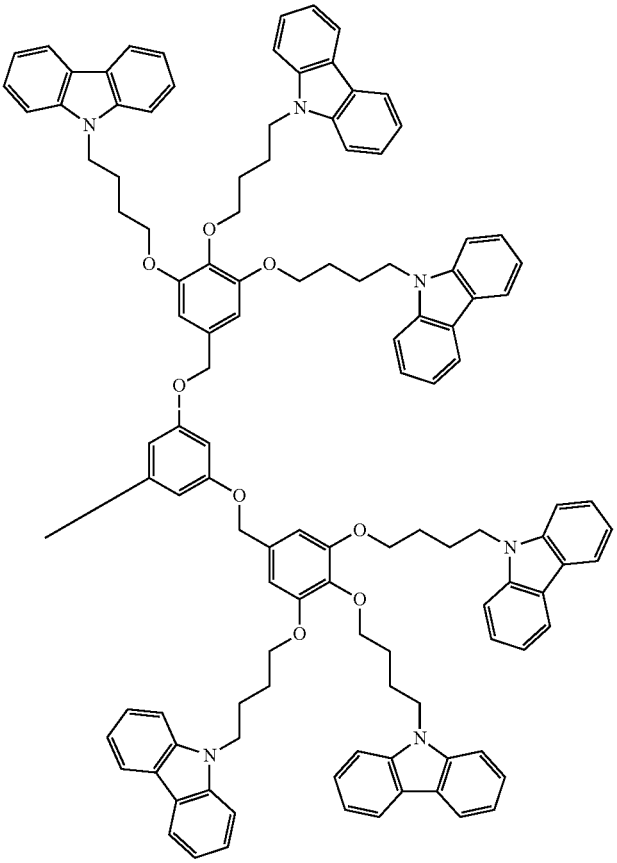 [SMILES: CCCc1cc(OCc2cc(OCCCCn3c4ccccc4c4ccccc43)c(OCCCCn3c4ccccc4c4ccccc43)c(OCCCCn3c4ccccc4c4ccccc43)c2)cc(OCc2cc(OCCCCn3c4ccccc4c4ccccc43)c(OCCCCn3c4ccccc4c4ccccc43)c(OCCCCn3c4ccccc4c4ccccc43)c2)c1]

The iridium phosphorescent dendrimer may emit red light.

The iridium phosphorescent dendrimer may be a homoleptic dendrimer in which an identical number of dendrons is tethered to each ligand. In another embodiment, each of the dendrons tethered to the ligand is identical. The Ir(III) complex core is completely encapsulated by a carbazole-based dendron, thereby maintaining photophysical properties of the Ir(III) complex core.

The iridium phosphorescent dendrimer of Formula 1 may be prepared by a method that includes contacting a tris-(2-benzo[b]thiophen-2-yl-nicotinic acid) Iridium (III) complex of Formula 5:

(5)

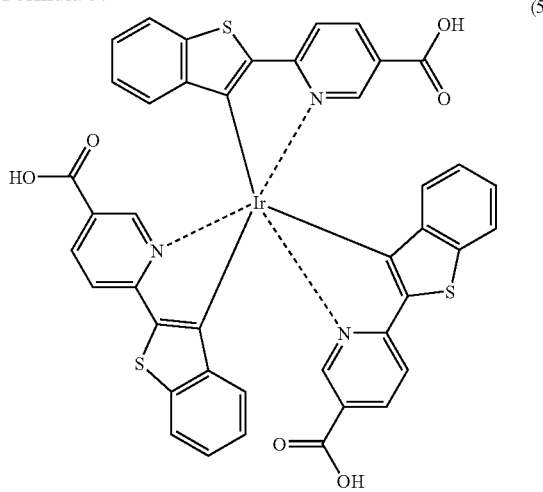

with carbazolyl alcohol.

Thus, the iridium phosphorescent dendrimer of Formula 1 may be prepared by mixing the tris-(2-benzo[b]thiophen-2-yl-nicotinic acid) Iridium (III) complex of Formula 5 with carbazolyl alcohol by catalyzed esterification.

In particular, the iridium phosphorescent dendrimer of Formula 1 may be prepared using a method that includes dissolving a tris-(2-benzo[b]thiophen-2-yl-nicotinic acid) Iridium (III) complex of Formula 5 and a carbazolyl alcohol in a solvent; adding a catalyst, for example 4-(dimethylamino) pyridinium p-toluenesulfonate ("DPTS") and 1,3-dicyclohexylcarbodiimide ("DCC") to a solution; stirring the solution under an inert atmosphere; and adding alcohol to the solution so as to form a precipitate.

Examples of the solvent of the method may include methylene chloride, chloroform, or the like or a combination thereof.

Examples of the alcohol used to form the precipitate may include methanol, ethanol, or the like or a combination thereof.

The tris-(2-benzo[b]thiophen-2-yl-nicotinic acid) Iridium (III) complex of Formula 5 may be prepared by contacting a compound of Formula 9:

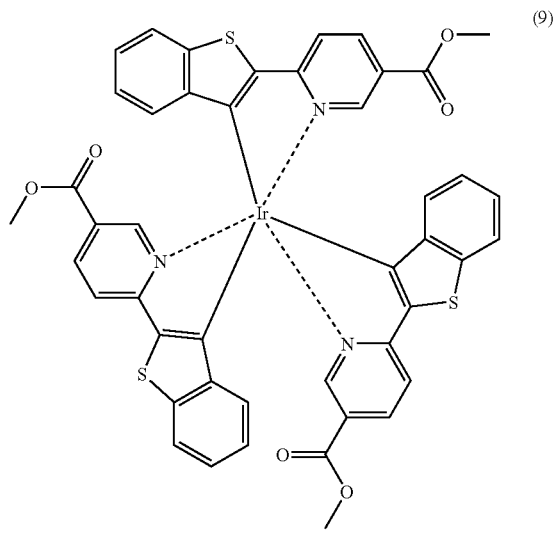

(9)

-continued

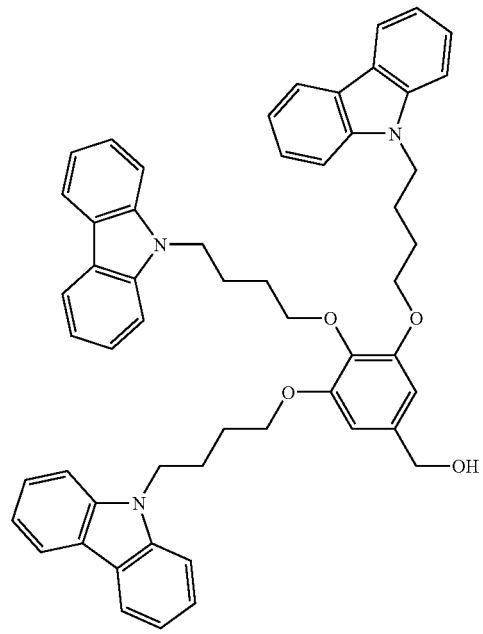

(11)

with lithium hydroxide monohydrate.

Figure 7:
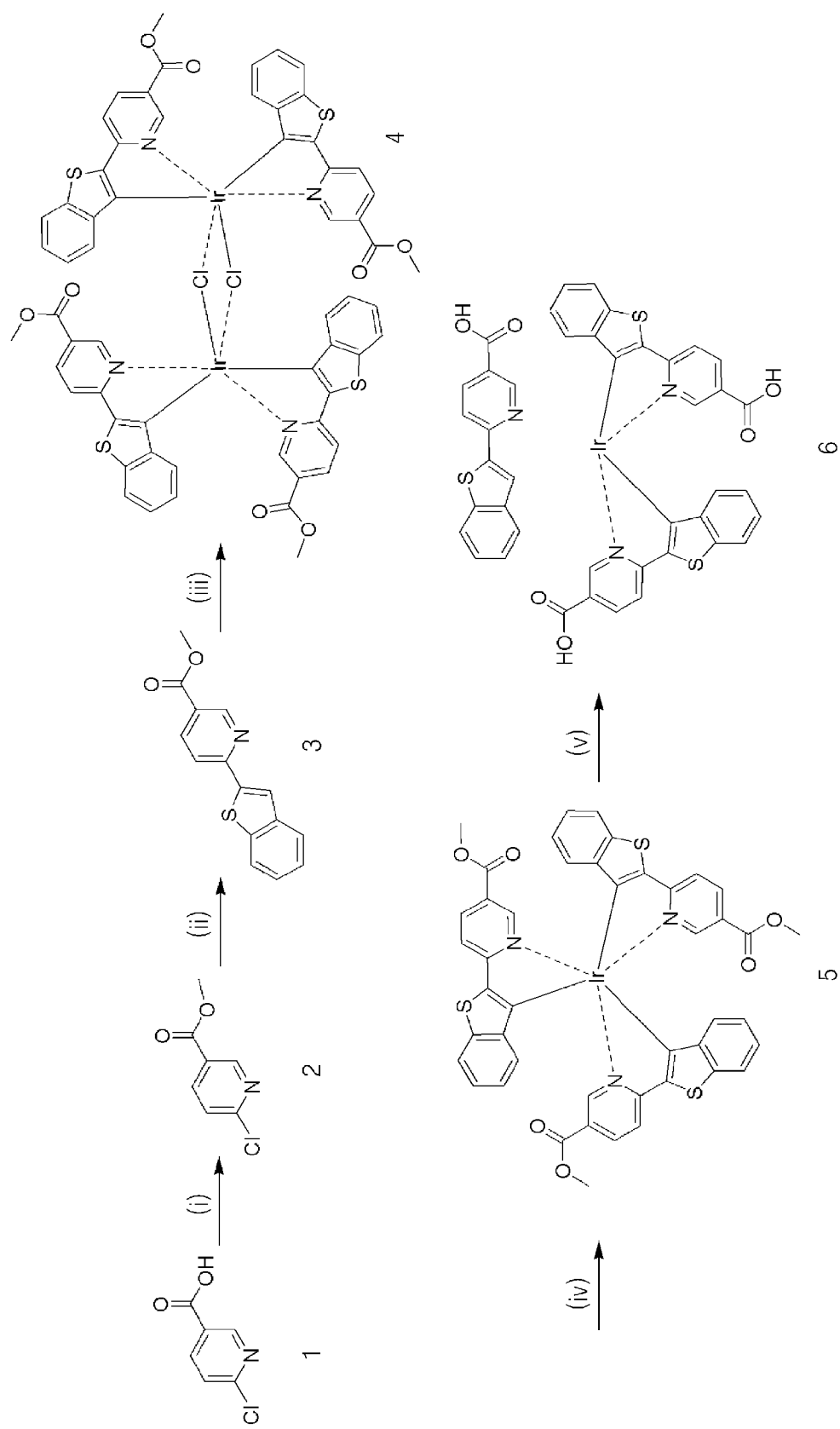
FIG. 7 is an exemplary embodiment of a method of preparing the tris-(2-benzo[b]thiophen-2-yl-nicotinic acid) Iridium (III) complex of Formula 5.

In particular, the tris-(2-benzo[b]thiophen-2-yl-nicotinic acid) Iridium (III) complex of Formula 5 may be prepared according to Reaction Scheme 1, which is shown in FIG. 7.

Added compounds and conditions in each operation of Reaction Scheme 1 as indicated in FIG. 7 are as follows: (i) MeOH, H$_2$SO$_4$, reflux; (ii) benzo[b]thiophene-2-yl-boronic acid, 2 N Na$_2$CO$_3$, tetrakis(triphenylphosphine)palladium (0), toluene:ethanol ("EtOH") (3:1, volume/volume ("v/v"); (iii) iridium(III) chloride hydrate, 2-ethoxyethanol:H$_2$O (3:1, v/v), 120° C.; (iv) 3,4,2-ethoxyethanol, silver trifluoroacetate, 110° C.; (v) LiOH/H$_2$O, tetrahydrofuran ("THF"):EtOH (3:1, v/v), reflux.

In particular, 2-benzo[b]thiophen-2-yl-nicotinic acid methylester (Compound 3 of Reaction Scheme 1) is synthesized by condensation of Compound 2 of Reaction Scheme 1 and benzo[b]thiophene-2-yl-boronic acid through the Suzuki coupling reaction. The IrCl$_3$3H$_2$O is treated with an excess of benzothiophene having pyridyl ligands in a mixed solvent of 2-ethoxyethanol and water (3:1 v/v) to efficiently form an iridium dimer (Compound 4 of Reaction Scheme 1) having a chloride bridge. Then, the chloride-bridged dimer is converted into Compound 5 of Reaction Scheme 1, followed by the conversion of the ester group into the carboxylic acid group.

The carbazolyl alcohol used in the method of preparing the iridium phosphorescent dendrimer may be represented by any one of Formulas 10, 11 and 12:

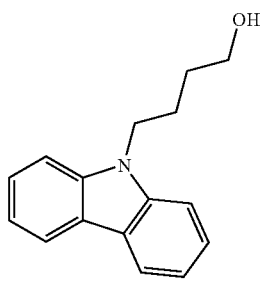

(10)

(12)

In particular, the iridium phosphorescent dendrimer of Formula 6 (a first-generation dendrimer) may be prepared by mixing the tris-(2-benzo[b]thiophen-2-yl-nicotinic acid) Iridium (III) complex of Formula 5 with the iridium phosphorescent dendrimer of Formula 10. The iridium phosphorescent dendrimer of Formula 7 (a second-generation dendrimer) may be prepared by mixing the tris-(2-benzo[b]thiophen-2-yl-nicotinic acid) Iridium (III) complex of Formula 5 with the iridium phosphorescent dendrimer of Formula 11. The iridium phosphorescent dendrimer of Formula 8 (a third-generation dendrimer) may be prepared by mixing the tris-(2-benzo[b]thiophen-2-yl-nicotinic acid) Iridium (III) complex of Formula 5 with the iridium phosphorescent dendrimer of Formula 12.

The first, second and third-generation iridium phosphorescent dendrimers prepared by the above method are emissive materials and may be prepared using a solution process. The iridium phosphorescent dendrimers may be effectively used in an electroluminescent device without a host.

An electroluminescent device according to an embodiment includes the iridium phosphorescent dendrimer of Formula 1.

In the electroluminescent device, the iridium phosphorescent dendrimer of Formula 1 may emit red light.

The electroluminescent device may include a structure of indium tin oxide ("ITO")/poly(3,4-ethylenedioxythiophene): poly(styrene sulfonate) ("PEDOT:PSS")/the phosphorescent dendrimer/2,9-dimethyl-4,7-diphenyl-1,10-phenanthroline ("BCP")/tris-(8-hydroxyquinoline) aluminum) ("Alq$_3$")/LiF/Al, wherein an oblique line is used to differentiate between layers in the device.

Hereinafter, one or more embodiments will be further described in detail with reference to the following examples. However, these examples are not intended to limit the purpose and scope of the disclosed embodiments.

All commercially available starting materials and solvents were purchased from Aldrich, TCI or Acros Co. and used without further purification, unless otherwise stated. HPLC-grade dimethylformamide ("DMF"), tetrahydrofuran ("THF"), and methylene chloride ("MC") were purchased from Samchun Chemical and distilled from CaH$_2$ immediately before use. All reactions were performed under an argon atmosphere unless otherwise stated.

Proton nuclear magnetic resonance ("$^1$H NMR") spectra were recorded on a Varian Mercury NMR 300 megahertz ("MHz") spectrometer using deuterated chloroform purchased from Cambridge Isotope Laboratories, Inc. $^{13}$C NMR spectra were recorded using a Varian Inova-500 spectrometer. Elemental analysis was performed by using an EA1112 elemental analyzer from Thermo Electron Corporation. Matrix-assisted laser desorption/ionization-time of flight ("MALDI-TOF") mass spectrometry was performed on a Voyager-DE STR MALDI-TOF mass spectrometer using a 2,5-dihydroxybenzoic acid ("DHB") matrix. Thermal properties were studied under a nitrogen atmosphere on a Mettler differential scanning calorimetry ("DSC") 821$^e$ and Mettler TGA 50. The redox properties of the synthesized compounds were examined by cyclic voltammetry using a Model EA161 potentiostat from eDAQ. Thin films of the compounds were coated on a platinum plate using chloroform as a solvent.

Preparation Example 1

Synthesis of Compound 6

(1) Methyl 6-chloronicotinate (Compound 2)

An oven-dried, 500 milliliter (mL) round bottom flask ("RBF") was charged with 6-chloronicotinic acid (compound 1) (14.4 grams (g), 91.3 millimole (mmol)), in 200 mL of freshly distilled MeOH. H$_2$SO$_4$ (1.22 mL, 22.8 mmol) was added dropwise to this mixture at room temperature. The mixture was stirred for 6 hours at 60° C. The organic phase was separated and extracted with ethyl acetate at pH 8. The organics were then combined and dried over Na$_2$SO$_4$. After filtering the mixture, the solvent was evaporated to obtain the crude product. The resulting crude product was then purified by silica gel column chromatography (eluent: methylene chloride:hexane=1:10 v/v) to yield 10.5 g (73%) of methyl 6-chloronicotinate (Compound 2).

$^1$H NMR (300 MHz, CDCl$_3$): chemical shift ("δ") (parts per million ("ppm")) 3.94 (singlet ("s"), 3H), 7.42 (doublet ("d"), coupling constant ("J")=7.2 hertz ("Hz"), 1H), 8.25 (d, J=7.8 Hz, 1H), 8.99 (s, 1H).

$^{13}$C NMR (125 MHz, CDCl$_3$): δ (ppm) 165.06, 164.06, 154.24, 147.46, 144.33, 142.77, 138.93, 135.38, 126.30, 125.35, 124.25, 123.19, 120.92, 117.62, 52.55.

Elemental analysis ("EA") for carbon, hydrogen and nitrogen ("CHN"): calculated for C$_7$H$_6$ClNO$_2$: C, 49.00; H, 3.52; N, 8.16. found: C, 50.01; H, 3.69; N, 8.34.

(2) Methyl 6-(benzo[b]thiophen-2-yl)nicotinate (Compound 3)

Compound 2 (5.0 g, 29.1 mmol), benzo[b]thiophene-2-ylboronic acid (6.23 g, 35.0 mmol), and tetrakis-(triphenylphosphine) palladium(0) (1.07 g, 0.87 mmol) were added to an RBF equipped with a reflux condenser and dissolved in a mixed solvent system of toluene (150 mL) and ethanol (50 mL). After addition of 50 mL of aqueous 2 N sodium carbonate solution, the reaction mixture was heated at 80° C. for 2 days. The organic phase was separated and extracted with methylene chloride. The organics were then combined, dried over Na$_2$SO$_4$ and filtered. The solvent was evaporated to give the crude product. The resulting crude product was then purified by silica gel column chromatography (eluent: ethyl acetate:methylene chloride=1:30 v/v) to yield 6.12 g (78%) of methyl 6-(benzo[b]thiophen-2-yl)nicotinate (Compound 3).

$^1$H NMR (300 MHz, CDCl$_3$): δ (ppm) 3.97 (s, 3H), 7.40 (d, J=7.50 Hz, 2H), 7.81~7.90 (multiplet ("m"), 3H), 7.91 (s, 1H), 8.34 (d, J=8.10 Hz, 1H), 9.21 (s, 1H).

$^{13}$C NMR (125 MHz, CDCl$_3$): δ (ppm) 165.74, 156.10, 151.26, 143.79, 141.45, 140.42, 137.88, 125.88, 124.92, 124.70, 124.60 123.28, 122.85, 119.07, 52.60.

EA for CHN: calculated for C$_{15}$H$_{11}$N$_2$O$_2$: C, 66.89; H, 4.12; N, 5.20. found: C, 66.76; H, 4.00; N, 4.94.

(3) i-Chloride-Ir(III) Dimer (Compound 4)

Compound 3 (3.0 g, 11.3 mmol) and iridium (III) chloride hydrate (1.60 g, 5.36 mmol) were dissolved in a mixed solvent system of ethoxyethanol (30 mL) and water (10 mL). The reaction mixture was stirred at 120° C. for 20 hours. Red precipitates were observed when the reaction mixture was cooled to room temperature. The red powder thus obtained was filtered and washed with H$_2$O and methanol. Then, the resulting crude product was recrystallized in methylene chloride to yield 2.54 g (62%) of i-chloride-Ir(III) dimer (Compound 4).

$^1$H NMR (300 MHz, CDCl$_3$): δ(ppm) 3.91 (s, 12H), 5.67 (d, J=8.4 Hz, 1H) 7.08 (t, J=7.5 Hz, 1H), 7.62 (d, J=8.1 Hz, 1H), 7.68 (d, J=8.1 Hz, 1H), 8.30 (d, J=7.8 Hz, 1H), 9.76 (s, 1H).

$^{13}$C NMR (125 MHz, CDCl$_3$): δ (ppm) 165.58, 164.06, 154.24, 147.46, 144.33, 142.77, 138.93, 135.38, 126.30, 125.35, 124.25, 123.19, 120.92, 117.62, 52.55.

EA for CHN: calculated for C$_{60}$H$_{40}$C$_{12}$Ir$_2$N$_4$O$_8$S$_4$: C, 47.14; H, 2.64; N, 3.67. found: C, 46.57; H, 2.69; N, 3.35.

(4) Tris-(2-benzo[b]thiophen-2-yl-nicotinate) Iridium (III) complex (Compound 5)

Compound 4 (0.90 g, 0.61 mmol), compound 3 (0.48 g, 1.83 mmol), and silver trifluoroacetate (0.3 g, 1.34 mmol) were dissolved in ethoxyethanol (30 mL). After degassing, the reaction mixture was stirred at 110° C. for 24 hours. Red precipitates were thus obtained when the reaction mixture was cooled down to room temperature. The red precipitates were filtered and were further washed with $H_2O$ and methanol. The resulting crude product was then purified by silica gel column chromatography (eluent: ethyl acetate:chloroform=1:50 v/v) to yield 0.80 g (66%) of Ir(III)-ester (Compound 5).

$^1$H NMR (300 MHz, $CDCl_3$): δ (ppm) 3.59 (s, 3H), 3.67 (s, 3H, $OCH_3$), 3.75 (s, 3H, $OCH_3$), 6.27 (t, J=6.3 Hz, 2H) 6.59 (d, J=8.4 Hz, 1H), 6.83 (t, J=8.1 Hz, 1H), 6.89 (m, 2H), 7.16~7.31 (m, 3H), 7.52 (d, J=8.4 Hz, 1H), 7.59 (d, J=8.4 Hz, 1H), 7.69 (d, J=8.4 Hz, 1H), 7.77~7.89 (m, 3H), 8.06 (d, J=8.6 Hz, 1H), 8.15~8.32 (m, 3H), 8.26 (s, 1H), 8.46 (s, 1H).

$^{13}$C NMR (125 MHz, $CDCl_3$): δ (ppm) 180.88, 180.85, 177.41, 170.07, 168.13, 167.09, 164.53, 164.43, 164.16, 160.33, 156.55, 153.29, 151.58, 147.75, 147.61, 147.28, 145.38, 144.96, 143.73, 139.35, 139.02, 138.65, 137.96, 136.72, 136.69, 132.68, 129.06, 127.06, 126.78, 126.45, 126.39, 124.38, 124.28, 123.22, 123.04, 122.99, 122.39, 121.98, 120.18, 118.66, 118.08, 117.22, 52.50, 52.47, 52.43.

EA for CHN: calculated for $C_{45}H_{30}IrN_3O_6S_3$: C, 54.20; H, 3.03; N, 4.21. found: C, 53.57; H, 3.01; N, 3.98.

(5) Tris-(2-benzo[b]thiophen-2-yl-nicotinic acid) Iridium (III) complex (Compound 6)

Compound 5 (0.60 g, 0.60 mmol) and lithium hydroxide monohydrate (0.19 g, 4.51 mmol) were dissolved in the mixed solvent system of THF:EtOH (3:1 v/v). After 2 hours, $H_2O$ (50 mL) was added to the mixture. The temperature was maintained at 80° C. for 24 hours. The organic mixture was extracted with ethyl acetate at pH 3. The organics were then combined, dried over $Na_2SO_4$, filtered and the solvent removed in vacuo. Then, the solid was crystallized in ethyl acetate and $CHCl_3$ to yield 0.54 g (94%) of Ir(III)-acid (Compound 6).

$^1$H NMR (300 MHz, $CDCl_3$): δ (ppm) 6.08 (d, J=8.1 Hz, 1H), 6.17 (d, J=8.1 Hz, 1H), 6.42 (d, J=8.1 Hz, 1H), 6.72 (t, J=7.8 Hz, 1H), 6.75~6.93 (m, 2H), 7.17 (t, J=7.8 Hz, 1H), 7.27 (m, 2H), 7.79 (d, J=8.4 Hz, 1H), 7.94~8.08 (m, 5H), 8.10~8.18 (m, 3H), 8.24~8.31 (m, 2H), 8.42 (s, 1H).

$^{13}$C NMR (125 MHz, $CDCl_3$): δ (ppm) 180.73, 180.25, 177.35, 170.93, 168.25, 167.76, 164.62, 164.61, 164.25, 160.82, 156.55, 154.86, 151.58, 147.75, 147.61, 147.28, 145.38, 144.77, 143.24, 139.35, 139.02, 138.08, 137.96, 136.72, 136.69, 132.68, 130.52, 127.06, 126.78, 126.45, 126.39, 124.38, 124.28, 123.22, 123.04, 122.99, 122.39, 121.92, 120.18, 118.66, 118.08, 117.22.

EA for CHN: calculated for $C_{42}H_{24}IrN_3O_6S_3$: C, 52.82; H, 2.53; N, 4.40. found: C, 52.50; H, 2.65; N, 4.35

Preparation Example 2

Synthesis of Carbazole-Based Dendron

Figure 8:
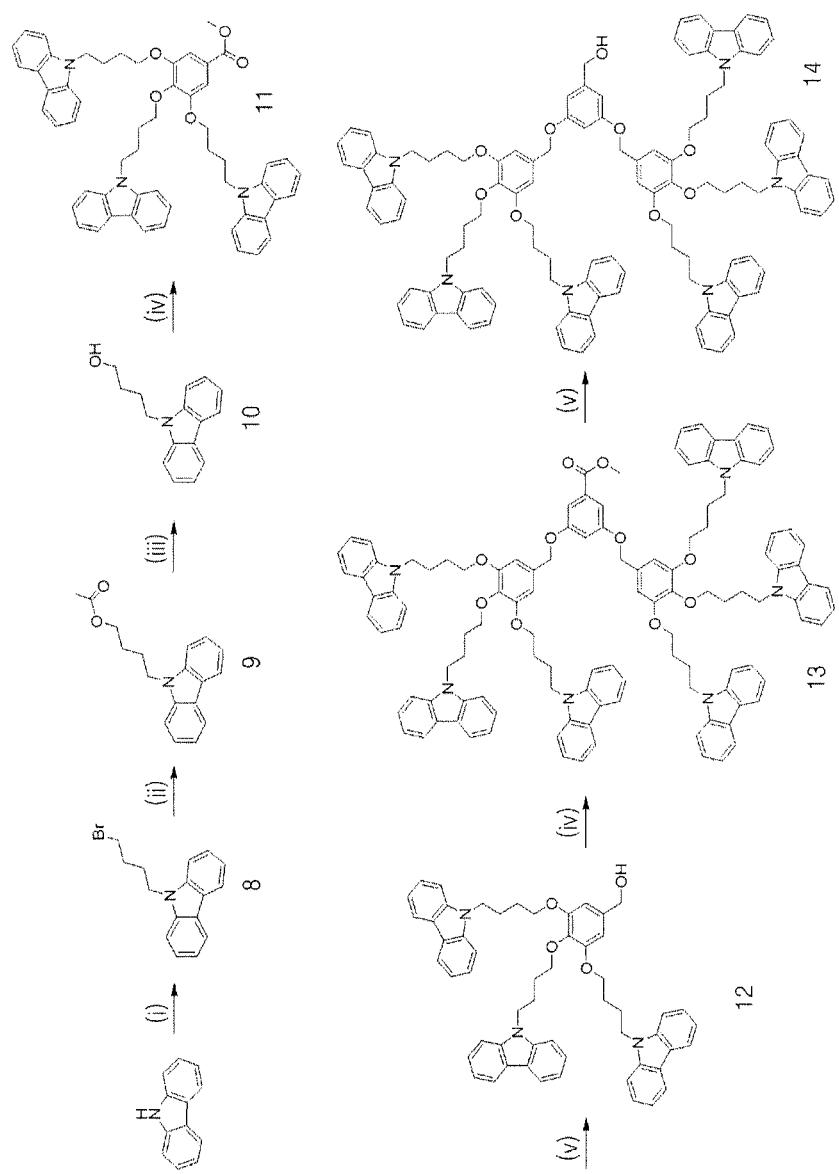
FIG. 8 is an exemplary embodiment of a method of preparing the carbazole-based dendron of Compounds 10, 12 and 14.

The carbazole-based dendron of Compounds 10, 12 and 14 may be prepared according to Reaction Scheme 2, which is shown in FIG. 8.

Added compounds and conditions in each operation of Reaction Scheme 2 as shown in FIG. 8 are as follows: (i) dibromobutane, NaH, MF; (ii) potassium acetate, DMF, 110° C.; (iii) LiOH, THF, reflux; (iv) methyl 3,4,5-trihydroxybenzoate, $K_2CO_3$, DMF, reflux; (v) $LiAlH_4$, THF, reflux, NaOH.

(1) 9-(4-Bromobutyl)-9H-carbazole (Compound 8)

1,4-Dibromobutane (640.2 g, 30 mol) and sodium hydride (30.1 g, 0.60 mol, 55%) were mixed in 500 mL of DMF under an argon atmosphere. Carbazole (100.0 g, 0.60 mol) was slowly added and the reaction mixture was stirred for 6 hours at room temperature. DMF was removed by vacuum distillation. Then, 9-(4-bromobutyl)-9H-carbazole was purified in a fresh column. The resulting product was purified by silica gel column chromatography (eluent: ethyl acetate:hexane=1:50 v/v) to yield 112 g (62%) of 9-(4-bromobutyl)-9H-carbazole (Compound 8).

$^1$H NMR (300 MHz, $CDCl_3$): δ (ppm) 1.9~1.99 (m, 2H), 2.01~2.07 (m, 2H), 3.40 (t, 2H), 4.33 (t, 2H), 7.25~7.32 (m, 2H), 7.41 (d, J=8.4 Hz, 2H), 7.46 (t, J=8.4 Hz, 2H), 8.15 (d, J=8.1 Hz, 2H).

$^{13}$C NMR (125 MHz, $CDCl_3$): δ (ppm) 130.82, 122.24, 120.15, 119.34, 118.95, 111.13, 59.93, 33.45, 30.57, 28.84.

EA for CHN: calculated for $C_{16}H_{16}BrN$: C, 63.59; H, 5.34; N, 4.63. found: C, 63.78; H, 5.63; N, 4.73.

(2) 4-(9H-Carbazol-9-yl)butyl acetate (Compound 9)

Compound 8 (40.1 g, 0.133 mol) and potassium acetate (19.5 g, 1.99 mol) were mixed in 300 mL of DMF under an argon atmosphere. The reaction mixture was stirred for 12 hours at 110° C. The organic phase was separated and extracted with ethyl acetate. The collected organics were then combined and dried over $Na_2SO_4$ and filtered. The solvent was evaporated to give the crude product. The resulting product was purified by silica gel column chromatography (eluent: ethyl acetate:methylene chloride=1:30 v/v) to yield 35 g (93%) of 4-(9H-carbazol-9-yl)butyl acetate (Compound 9).

$^1$H NMR (300 MHz, $CDCl_3$): δ (ppm) 1.68~1.76 (m, 2H), 1.94~1.98 (m, 2H), 202 (s, 3H), 4.06 (t, 2H), 4.38 (t, 2H), 7.27~7.32 (m, 2H), 7.41 (d, J=8.4 Hz, 2H), 7.50 (t, J=8.1 Hz, 2H), 8.12 (d, J=8.4 Hz, 2H).

$^{13}$C NMR (125 MHz, $CDCl_3$): δ (ppm) 170.68, 130.85, 122.36, 120.15, 119.53, 118.84, 111.48, 64.69, 60.83, 26.57, 25.78, 20.74.

EA for CHN: calculated for $C_{18}H_{19}NO_2$: C, 76.84; H, 6.81; N, 4.98. found: C, 77.18; H, 6.61; N, 4.85.

(3) 4-(9H-Carbazol-9-yl)butan-1-ol (Compound 10)

Compound 9 (35.1 g, 0.125 mol) and lithium hydroxide monohydrate (13.0 g, 0.31 mol) were dissolved in 200 mL THF. The reaction mixture was stirred at 80° C. for 12 hours. The mixture was filtered and the homogeneous solution was evaporated to give the crude product. The resulting product was purified by silica gel column chromatography (eluent: ethyl acetate:methylene chloride=1:10 v/v) to yield 26 g (86%) of 4-(9H-carbazol-9-yl)butan-1-ol (Compound 10).

$^1$H NMR (300 MHz, $CDCl_3$): δ (ppm) 1.24 (s, 1H), 1.60~1.65 (m, 2H), 1.95~1.99 (m, 2H), 3.64 (t, 2H), 4.37 (t, 2H), 7.21~7.26 (m, 2H), 7.43 (d, J=8.4 Hz, 2H), 7.50 (t, J=8.1 Hz, 2H), 8.12 (d, J=8.4 Hz, 2H).

$^{13}$C NMR (125 MHz, $CDCl_3$): δ (ppm) 131.55, 123.56, 121.63, 119.93, 119.04, 111.68, 62.89, 60.85, 29.07, 26.53.

EA for CHN: calculated for $C_{16}H_{17}NO$: C, 80.30; H, 7.16; N, 5.85. found: C, 80.26; H, 7.34; N, 5.73.

(4) Methyl 3,4,5-tris(4-(9H-carbazol-9-yl)butoxy) benzoate (Compound 11)

Compound 10 (20.0 g, 66.2 mmol); methyl 3,4,5-trihydroxybenzoate (3.68 g, 22.0 mmol); and potassium carbonate (9.0 g, 66.2 mmol) were mixed in 100 mL of DMF under an argon atmosphere. The organic phase was separated and extracted with methylene chloride. The organics were then combined and dried over $Na_2SO_4$ followed by filtration. The solvent was evaporated to give the crude product, which was purified by silica gel column chromatography (eluent: ethyl acetate:methylene chloride=1:30 v/v) to yield 16 g (85%) of methyl 3,4,5-tris(4-(9H-carbazol-9-yl)butoxy)benzoate (Compound 11).

$^1$H NMR (300 MHz, CDCl$_3$): δ (ppm) 1.69~1.77 (m, 6H), 1.94~2.04 (m, 6H), 3.81 (t, 2H), 3.84 (s, 3H), 3.91 (t, 4H), 4.12 (t, 2H), 4.19 (t, 4H), 7.16 (s, 2H), 7.18 (t, J=8.4 Hz, 6H), 7.30~7.34 (m, 6H), 7.39 (t, J=8.4 Hz, 6H), 8.07 (d, J=8.4 Hz, 6H).

$^{13}$C NMR (125 MHz, CDCl$_3$): δ (ppm) 165.94, 153.17, 140.82, 140.47, 138.38, 136.39, 125.78, 125.73, 122.97, 122.93, 120.51, 120.49, 118.97, 118.91, 108.93, 108.80, 105.40, 72.85, 68.71, 65.53, 51.54, 42.66, 27.91, 27.22, 25.99, 25.96.

EA for CHN: calculated for C$_{56}$H$_{53}$N$_3$O$_5$: C, 79.31; H, 6.30; N, 4.95. found: C, 79.46; H, 6.52; N, 5.04.

(5) (3,4,5-Tris(4-(9H-carbazol-9-yl)butoxy)phenyl) methanol (Compound 12)

An oven-dried, magnetically stirred, 500 mL RBF was charged with a solution of LiAlH$_4$ (2.2 g, 0.038 mol) in 100 mL freshly distilled THF. Then, THF solution of compound 11 (15.0 g, 0.023 mol) was added dropwise over 0.5 hours. After the reaction was maintained for 2 hours at 80° C., 1 N NaOH was slowly added. The organic phase was separated and extracted with chloroform. The organics were then dried over Na$_2$SO$_4$ and filtered. The solvent was evaporated to give the crude product. The resulting crude product was then purified by silica gel column chromatography (eluent: chloroform:ethyl acetate=1:50 v/v) to yield 13.2 g (92%) of (3,4,5-tris(4-(9H-carbazol-9-yl)butoxy)phenyl)methanol (Compound 12).

$^1$H NMR (300 MHz, CDCl$_3$): δ (ppm) 1.71~1.78 (m, 6H), 1.95~2.02 (m, 6H), 3.82 (t, 2H), 3.90 (t, 4H), 4.14 (t, 2H), 4.21 (t, 4H), 4.52 (s, 1H, OH), 6.45 (s, 2H), 7.19 (t, J=8.4 Hz, 6H), 7.32 (m, 6H), 7.40 (t, J=8.4 Hz, 6H), 8.08 (d, J=8.4 Hz, 6H).

$^{13}$C NMR (125 MHz, CDCl$_3$): δ (ppm) 153.01, 140.49, 140.47, 137.17, 136.53, 125.78, 125.73, 122.97, 122.93, 120.51, 120.49, 118.97, 118.91, 108.93, 108.80, 105.40, 72.85, 68.71, 65.53, 42.836, 42.66, 27.91, 27.22, 25.99, 25.96.

EA for CHN: calculated for C$_{55}$H$_{53}$N$_3$O$_4$: C, 80.56; H, 6.51; N, 5.12. found: C, 80.69; H, 6.65; N, 5.14.

(6) Methyl 3,5-bis(3,4,5-tris(4-(9H-carbazol-9-yl) butoxy)benzyloxy)benzoate (Compound 13)

To an RBF was added compound 12 (2.00 g, 2.44 mmol); methyl 3,5-dihydroxybenzoate (185 mg, 1.10 mmol); tributylphosphine (2.96 g, 14.6 mmol); and N, N-diisopropylethylamine ("DIEA") (1.89 g, 14.6 mmol) in THF (300 mL). Diisopropylazodicarboxylate ("DIAD") (2.90 mL, 14.6 mmol) was added dropwise to the reaction mixture over a period of 10 min. The reaction mixture was stirred at room temperature for 3 days. The organic phase was separated and extracted with methylene chloride. The organics were then dried over Na$_2$SO$_4$ and filtered. The solvent was evaporated to give the crude product. It was purified by silica gel column chromatography (eluent: hexane:methylene chloride=1:50 v/v) to yield 2.38 g (55%) of methyl 3,5-bis(3,4,5-tris(4-(9H-carbazol-9-yl)butoxy)benzyloxy)benzoate (Compound 13).

$^1$H NMR (300 MHz, CDCl$_3$): δ (ppm) 1.67~1.72 (m, 12H) 1.89~1.94 (m, 12H) 3.8~3.87 (m, 15H), 4.18~4.22 (m, 12H), 4.87 (s, 4H), 6.69 (s, 1H), 7.12 (s, 2H), 7.18 (t, J=8.4 Hz, 12H), 7.26~7.34 (m, 12H), 7.39 (t, J=8.4 Hz, 12H), 7.63 (d, J=7.5 Hz, 2H) 8.06 (d, J=8.4 Hz, 12H).

$^{13}$C NMR (125 MHz, CDCl$_3$): δ (ppm) 166.77, 159.81, 154.88, 153.02, 140.42, 140.39, 137.63, 132.19, 131.74, 129.40, 125.73, 125.69, 122.90, 122.88, 121.61, 120.46, 120.44, 118.93, 118.87, 108.87, 108.73, 108.41, 107.34, 106.26, 72.78, 70.54, 68.67, 52.41, 42.74, 42.54, 29.83, 27.85, 27.11, 25.90, 25.87.

EA of CHN: calculated for C$_{118}$H$_{110}$N$_6$O$_{10}$C, 79.97; H, 6.26; N, 4.74. found: C, 80.32; H, 6.17; N, 4.78.

(7) (3,5-Bis(3,4,5-tris(4-(9H-carbazol-9-yl)butoxy) benzyloxy)phenyl)methanol (Compound 14)

An oven-dried, magnetically stirred, 100 mL RBF was charged with a solution of LiAlH$_4$ (9 mg, 0.141 mmol) in 40 mL freshly distilled THF. Then, a THF solution of compound 13 (0.17 g, 0.0564 mmol) was added dropwise over 0.5 hours. After stirring the reaction mixture for 2 hours at 80° C., 1 N NaOH was slowly added. The organic phase was separated and extracted with chloroform. The organics were then dried over Na$_2$SO$_4$ and filtered. The solvent was evaporated to give the crude product. The resulting crude product was then purified by silica gel column chromatography (eluent: chloroform:ethyl acetate=1:50 v/v) to yield 0.14 g (76%) of (3,5-bis(3,4,5-tris(4-(9H-carbazol-9-yl)butoxy)benzyloxy) phenyl)methanol (Compound 14).

$^1$H NMR (300 MHz, CDCl$_3$): δ (ppm) 1.65~1.71 (m, 12H), 1.90~1.96 (m, 12H), 3.81~3.88 (m, 12H), 4.15~4.21 (m, 12H), 4.60 (s, 2H), 4.84 (s, 4H), 6.48 (s, 4H), 6.59 (s, 1H), 7.17 (t, J=8.4 Hz, 12H), 7.25~7.32 (m, 12H), 7.38 (t, J=8.4 Hz, 12H), 7.61 (d, J=7.5 Hz, 2H) 8.05 (d, J=8.4 Hz, 12H).

$^{13}$C NMR (125 MHz, CDCl$_3$): δ (ppm) 160.21, 154.95, 153.06, 143.62, 140.47, 140.44, 137.60, 132.18, 129.48, 125.76, 125.73, 122.95, 122.95, 121.70, 120.50, 118.97, 118.91, 108.91, 108.77, 106.25, 105.75, 101.38, 72.84, 70.37, 68.73, 65.34, 42.81, 42.62, 27.90, 27.17, 25.96, 25.92.

EA for CHN: calculated for C$_{117}$H$_{110}$N$_6$O$_9$: C, 80.57; H, 6.36; N, 4.82. found: C, 80.74; H, 6.15; N, 4.86.

Examples 1 to 3

Synthesis of Iridium Phosphorescent Dendrimers

Figure 9A:
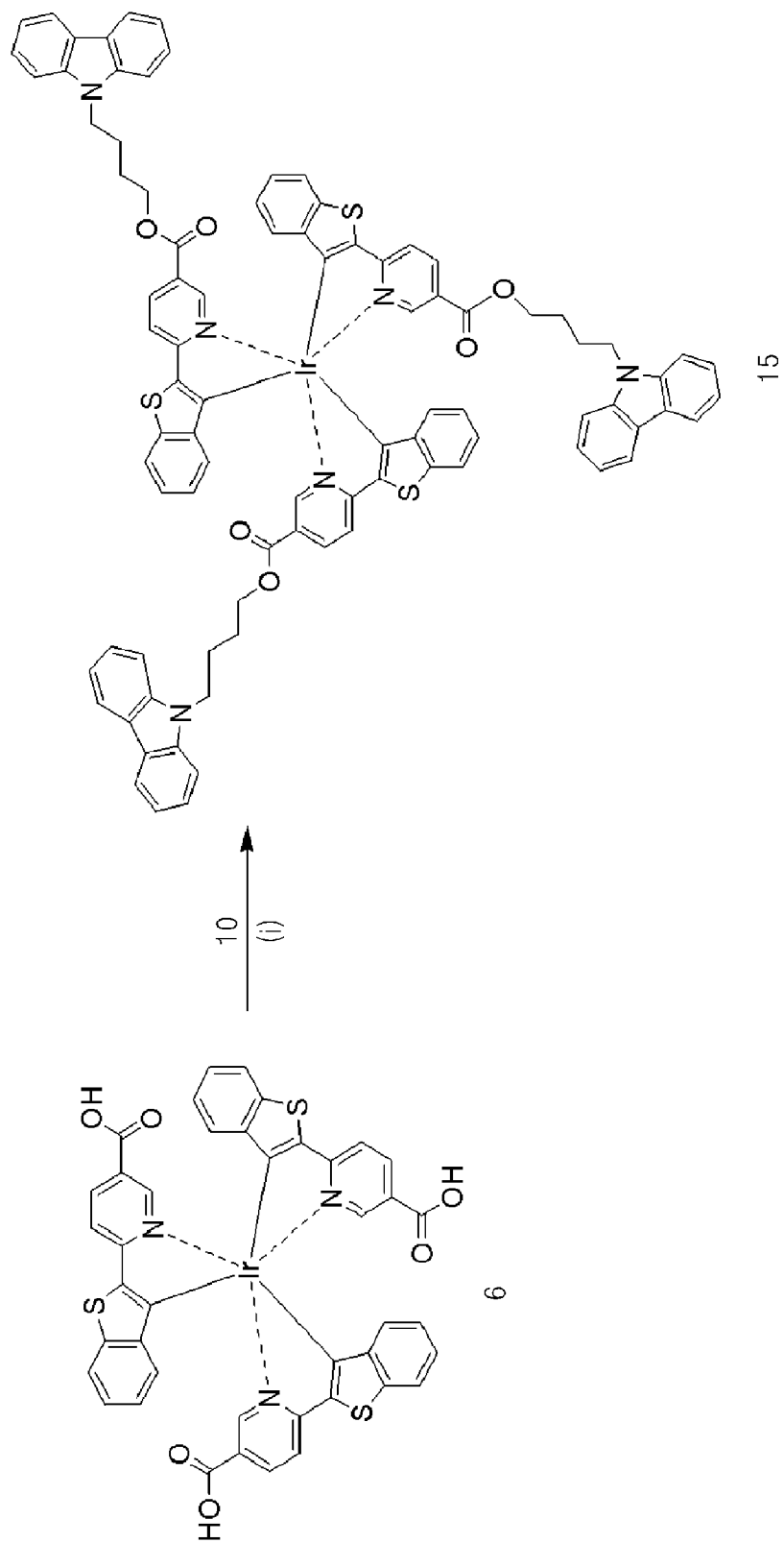
FIG. 9A is an exemplary embodiment of a method of preparing the iridium phosphorescent dendrimer of Compound 15.
Figure 9B:
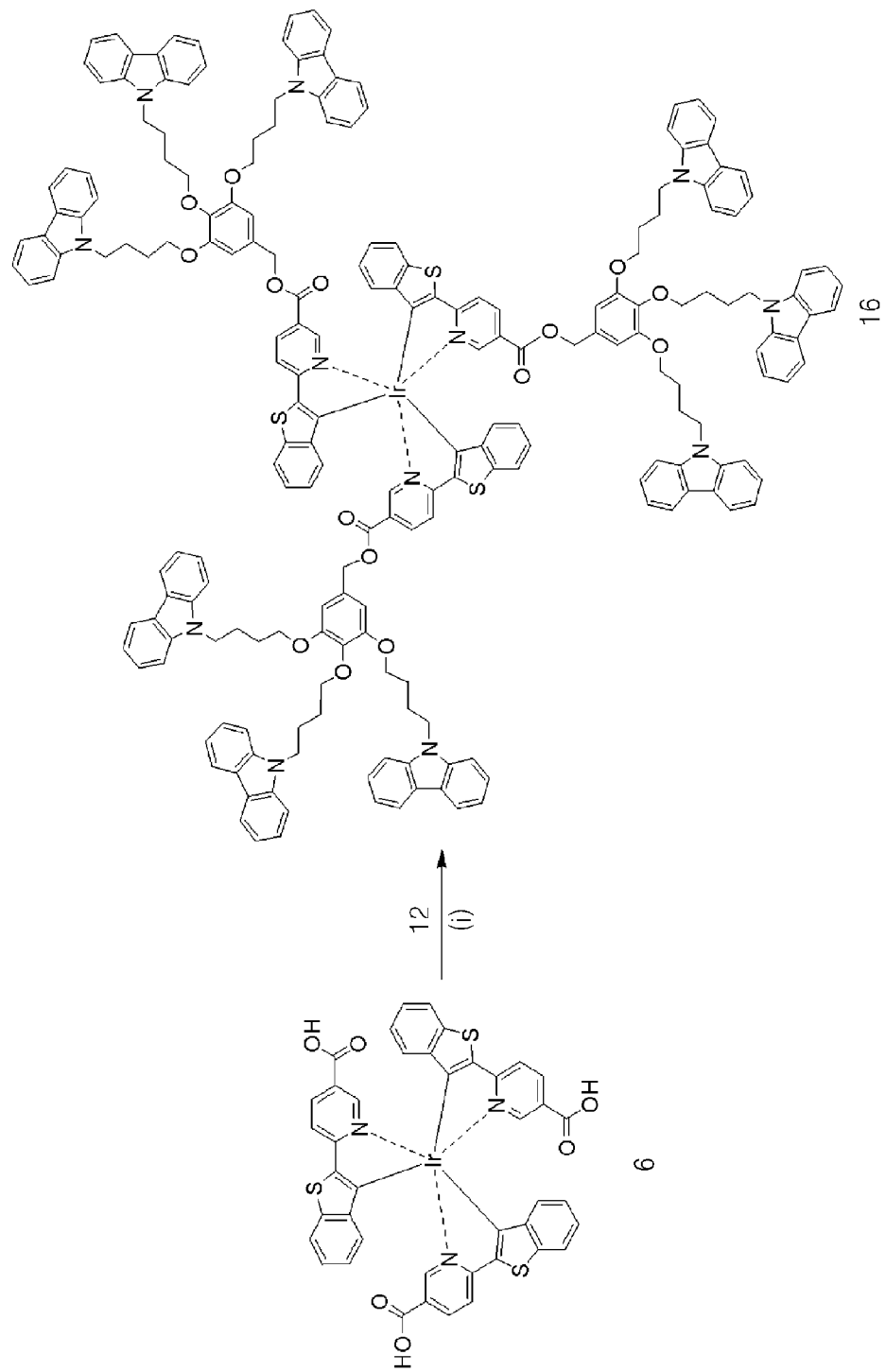
FIG. 9B is an exemplary embodiment of a method of preparing the iridium phosphorescent dendrimer of Compound 16.
Figure 9C:
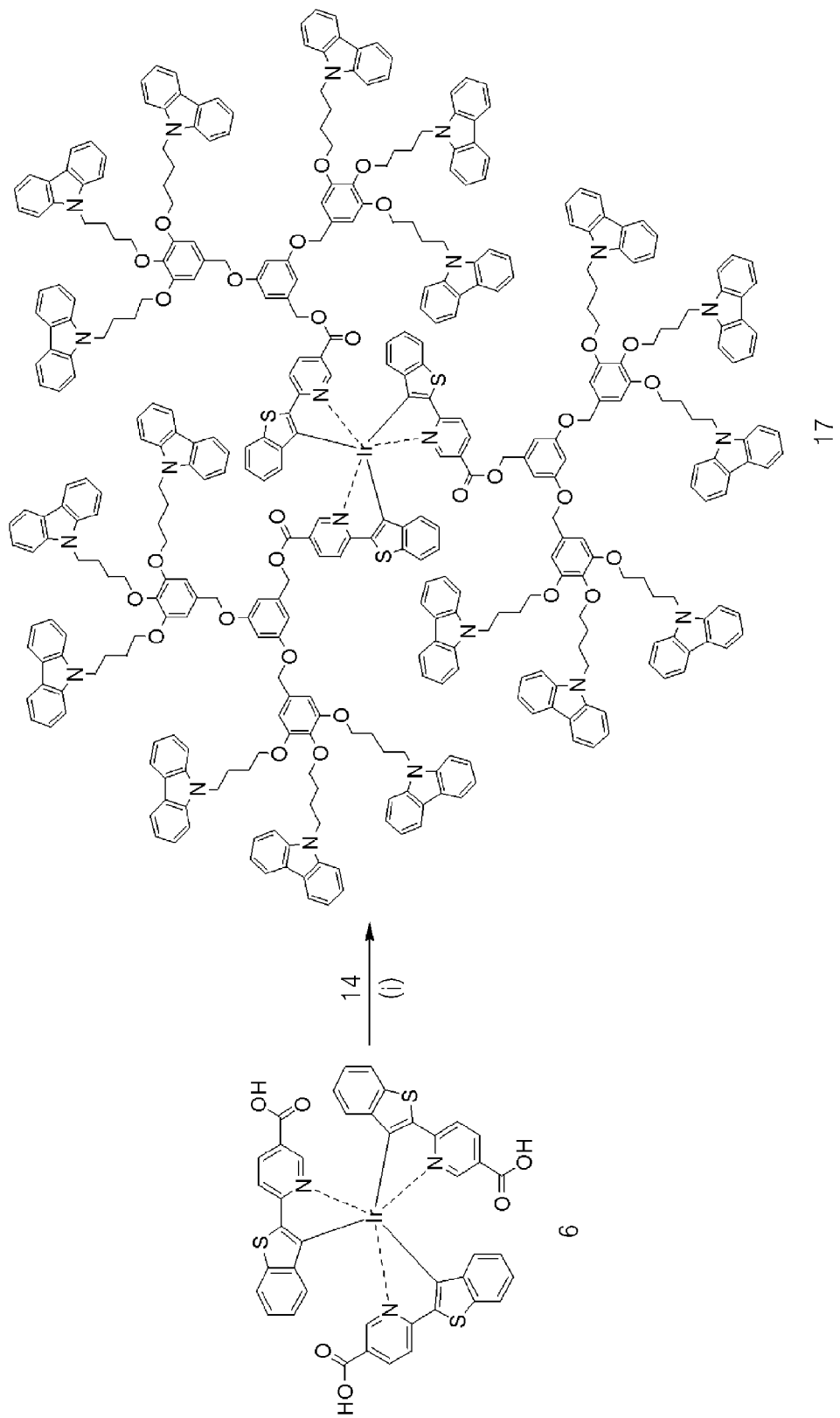
FIG. 9C is an exemplary embodiment of a method of preparing the iridium phosphorescent dendrimer of Compound 17.

Iridium phosphorescent dendrimers of Compounds 15, 16 and 17 are prepared according to the reaction schemes shown in FIGS. 9A to 9C, respectively.

Added compounds and conditions in each operation of the reaction schemes shown in FIGS. 9A to 9C are as follows: (i) DPTS, DCC, methylene chloride, room temperature.

Example 1

First-Generation Dendrimer (Compound 15)

Compound 6 (0.20 g, 0.209 mmol) and compound 10 (0.20 g, 0.838 mmol) were dissolved in 50 mL methylene chloride.

4-(Dimethylamino)pyridinium p-toluenesulfonate (DPTS, 0.18 g, 0.628 mmol) and 0.30 g of 1,3-dicyclohexylcarbodiimide (DCC, 1.47 mmol) were added to the methylene chloride solution. The reaction mixture was stirred at room temperature for 24 hours under an argon atmosphere. Repeated dissolution and filtration removed most of the resultant urea. The filtered methylene chloride solution was then added dropwise to methanol under vigorous stirring. The precipitate was collected and the resulting product was purified by silica gel column chromatography (eluent: ethyl acetate:chloroform=1:40) to yield 0.15 g (43%) of a red solid.

$^1$H NMR (300 MHz, CDCl$_3$): δ (ppm) 1.21~1.28 (m, 2H), 1.30~1.37 (m, 2H), 1.45~1.51 (m, 2H), 1.58~1.62 (m, 2H), 1.64~1.68 (m, 2H), 1.80~1.86 (m, 2H), 3.84~3.89 (m, 2H), 4.06~4.10 (m, 2H), 4.11~4.14 (m, 2H), 4.15~4.19 (m, 2H), 4.21~4.26 (m, 2H), 4.27~4.31 (m, 2H), 6.21 (d, J=8.1 Hz, 2H), 6.56 (d, J=8.1 Hz, 1H), 6.72 (t, J=7.8 Hz, 1H), 6.85~6.91 (m, 2H), 7.07~7.11 (m, 3H), 7.18~7.23 (m, 2H), 7.22~7.27 (m, 6H), 7.28~7.32 (m, 6H), 7.41~7.46 (m, 6H), 7.59~7.63 (m, 2H), 7.79 (d, J=8.1 Hz, 1H), 7.85 (d, J=8.4 Hz, 1H), 7.93 (d, J=8.1 Hz, 1H), 8.04 (s, 1H), 8.12~8.16 (m, 6H), 8.45 (s, 1H).

$^{13}$C NMR (125 MHz, CDCl$_3$): δ (ppm) 180.92, 177.19, 169.93, 168.03, 166.92, 163.87, 163.75, 163.56, 160.27, 156.37, 152.98, 151.22, 147.70, 147.57, 147.20, 145.25, 144.89, 143.73, 140.53, 140.46, 139.47, 138.97, 138.87, 137.92, 136.69, 132.66, 129.03, 127.01, 126.69, 126.47, 126.35, 125.98, 125.88, 125.86, 124.38, 124.26, 123.22, 123.15, 123.13, 123.07, 122.99, 122.90, 122.28, 122.06, 120.73, 120.69, 120.67, 120.14, 119.21, 119.15, 119.11, 118.52, 118.10, 117.18, 108.74, 64.72, 64.65, 42.62, 42.58, 42.54, 26.40, 26.15, 26.00, 25.61, 25.55, 25.36.

MALDI-TOF MS exact mass calculated for C$_{90}$H$_{69}$IrN$_6$O$_6$S$_3$ [M$^+$] 1618.4070. found 1618.2455.

EA for CHN calculated for C$_{90}$H$_{69}$IrN$_6$O$_6$S$_3$; C, 66.77; H, 4.30; N, 5.19. found: C, 67.96; H, 4.25; N, 5.02.

Example 2

Second-Generation Dendrimer (Compound 16)

Compound 6 (0.15 g, 0.157 mmol) and compound 12 (0.515 g, 0.628 mmol) were dissolved in 50 mL CH$_2$Cl$_2$. DPTS (0.14 g, 0.471 mmol) and 0.23 g of DCC (1.10 mmol) were added to the mother solution. The reaction mixture was allowed to stir at room temperature for 24 hours under an argon atmosphere. Repeated dissolution and filtration removed most of the resultant urea. The filtered methylene chloride solution was then added dropwise to vigorously stirred methanol. The precipitate was collected and the resulting product was purified by silica gel column chromatography (eluent: ethyl acetate:chloroform 1:40) to yield 0.3 g (57%) of a red solid.

$^1$H NMR (300 MHz, CDCl$_3$): δ (ppm) 1.7~1.80 (m, 18H), 2.0~22.08 (m, 18H), 3.91~3.95 (m, 18H), 4.27~4.31 (m, 18H), 4.98~5.02 (m, 6H), 6.28 (s, 2H), 6.34 (s, 2H), 6.41 (s, 2H), 6.61 (d, J=8.1 Hz, 1H), 6.72 (t, J=7.8 Hz, 1H), 6.79 (t, J=8.4 Hz, 1H), 6.87 (t, J=8.1 Hz, 1H), 7.05~7.09 (m, 2H), 7.15~7.17 (m, 1H), 7.28~7.30 (m, 18H), 7.38~7.41 (m, 18H), 7.46~7.49 (m, 18H), 7.63 (d, J=8.1 Hz, 1H), 7.69 (d, J=8.4 Hz, 1H), 7.75 (d, J=8.4 Hz, 1H), 8.02 (d, J=8.4 Hz, 1H), 8.04 (d, J=8.4 Hz, 1H), 8.10 (s, 1H), 8.1~28.15 (m, 18H), 8.26 (s, 1H), 8.53 (s, 1H).

$^{13}$C NMR (125 MHz, CDCl$_3$): δ (ppm) 177.49, 169.97, 168.06, 166.78, 163.80, 163.54, 163.35, 156.64, 153.02, 152.87, 147.47, 147.33, 147.16, 145.18, 144.65, 143.78, 140.48, 140.47, 139.32, 138.71, 138.64, 138.04, 137.97, 137.84, 137.71, 132.63, 130.66, 130.57, 130.40, 128.74, 126.65, 126.36, 125.81, 125.79, 125.76, 125.73, 124.06, 123.19, 122.98, 122.95, 122.93, 122.75, 122.25, 121.79, 120.54, 120.49, 119.91, 119.03, 119.01, 118.95, 117.85, 117.09, 108.90, 108.80, 107.67, 107.05, 106.99, 72.90, 72.80, 68.78, 68.68, 67.31, 42.82, 42.67, 27.95, 27.25, 26.11, 26.00, 25.96.

MALDI-TOF MS exact mass calculated for C$_{207}$H$_{177}$IrN$_{12}$O$_{15}$S$_3$ [M$^+$] 3359.2248. found 3361.1160.

EA for CHN: calculated for C$_{207}$H$_{177}$IrN$_{12}$O$_{15}$S$_3$: C, 73.97; H, 5.31; N, 5.00. found: C, 74.56; H, 5.36; N, 4.97

Example 3

Third-Generation Dendrimer (Compound 17)

Compound 6 (0.15 g, 0.157 mmol) and compound 14 (1.11 g, 0.628 mmol) were dissolved in 50 mL CH$_2$Cl$_2$. DPTS (0.14 g, 0.471 mmol) and 0.23 g of DCC (1.10 mmol) were added to the CH$_2$Cl$_2$ solution. The mixture was stirred at room temperature for 24 hours under an argon atmosphere. Repeated dissolution and filtration removed most of the resulting urea. The filtered solution was then added dropwise to methanol while stirring vigorously. The precipitate was collected and the resulting product was purified by silica gel column chromatography (eluent: ethyl acetate:chloroform 1:40) to yield 0.4 g (42%) of a red solid.

$^1$H NMR (300 MHz, CDCl$_3$): δ (ppm) 1.65~1.72 (m, 36H), 1.96~1.99 (m, 36H), 3.86~3.90 (m, 36H), 4.17~4.21 (m, 36H), 4.86~4.89 (m, 12H), 5.09~5.12 (m, 6H), 6.27 (t, J=7.8 Hz, 2H), 6.34 (s, 1H), 6.48 (s, 1H), 6.55~6.57 (m, 5H), 6.72 (t, J=7.8 Hz, 1H), 6.79 (t, J=8.4 Hz, 1H), 6.87 (t, J=8.1 Hz, 1H), 7.05~7.09 (m, 2H), 7.14~7.18 (m, 1H), 7.23~7.25 (m, 36H), 7.29~7.32 (m, 36H), 7.40~7.42 (m, 36H), 7.63 (d, J=8.1 Hz, 1H), 7.69 (d, J=8.4 Hz, 1H), 7.75 (d, J=8.4 Hz, 1H), 8.02 (d, J=8.4 Hz, 1H), 8.04 (d, J=8.1 Hz, 1H), 8.10 (s, 1H), 8.11~8.13 (m, 36H), 8.27 (s, 1H), 8.57 (s, 1H).

$^{13}$C NMR (125 MHz, CDCl$_3$): δ (ppm) 178.21, 176.24, 170.23, 168.54, 167.67, 164.25, 164.15, 164.02, 160.21, 160.11, 156.37, 153.87, 153.09, 151.47, 147.54, 147.45, 147.03, 145.24, 144.67, 143.89, 143.57, 140.47, 140.41, 139.78, 139.67, 139.24, 138.98, 138.62, 137.75, 136.47, 132.54, 131.93, 129.04, 127.47, 126.96, 126.78, 126.54, 126.38, 125.75, 124.68, 124.57, 123.24, 123.14, 122.98, 122.95, 122.93, 122.24, 121.95, 121.70, 120.54, 120.49, 118.97, 118.93, 118.75, 108.91, 108.76, 108.02, 107.57, 107.02, 106.46, 72.87, 70.48, 68.77, 42.80, 42.57, 27.91, 27.15, 25.93.

EA for CHN: calculated for C$_{393}$H$_{348}$IrN$_{21}$O$_{30}$S$_3$: C, 76.96; H, 5.72; N, 4.80. found: C, 77.56; H, 5.75; N, 4.75.

Examples 4 to 6

Characterization of Iridium Phosphorescent Dendrimers

Example 4

Thermal Analysis of Phosphorescent Dendrimer

The thermal properties of the phosphorescent dendrimer prepared in Examples 1 to 3 were investigated by using differential scanning calorimetry ("DSC") and thermogravimetric analysis ("TGA") under a nitrogen atmosphere.

Figure 1B:
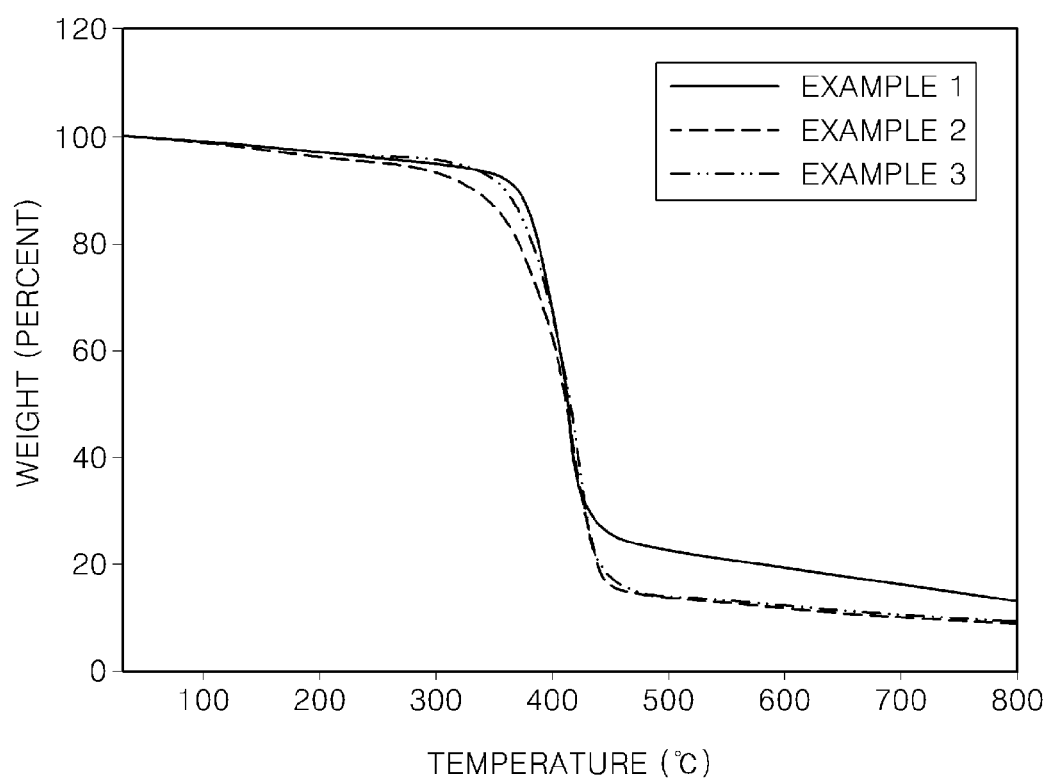
FIG. 1B is a thermogravimetric analysis ("TGA") thermogram illustrating weight percent (%) versus temperature (° C.) of phosphorescent dendrimers prepared according to Examples 1 to 3 and analyzed according to Example 4.

FIG. 1A is a DSC thermogram of the phosphorescent dendrimers prepared according to Examples 1 to 3. FIG. 1B is a TGA thermogram of the phosphorescent dendrimers prepared in Examples 1 to 3. Referring to FIG. 1A, no discernible melting behavior was observed up to 290° C. in the DSC thermograms of the three dendrimers. As the density of the carbazolyl branch dendron increased, the glass transition temperatures decreased due to the increment of the plasticization effect. Referring to FIG. 1B, in the TGA thermogram of each dendrimer, no significant weight loss was observed up to 310° C. The onset temperatures of primary decomposition were above 315° C. in all cases (see Table 1). All the dendrimers exhibited good thermal stability. These results show that the attachment of the carbazole dendrons to the core-iridium complexes did not have a detrimental effect on the thermal stability of the iridium (III) complex.

Example 5

Absorption and Photoluminescence Spectroscopy

A 3 weight percent (wt %) solution of each dendrimer in chloroform was filtered through an ACRODISC syringe filter (Millipore, 0.2 micrometer (μm)) and subsequently spin-cast on a quartz substrate. The films were then dried overnight at 80° C. for 48 hours under vacuum.

Absorption spectra of the films and chloroform solutions, having a concentration of $1\times10^{-5}$ moles per liter (M) were obtained using a HP 8453 PDA type UV-vis spectrometer in the wavelength range of about 190 to about 1100 nanometers (nm). Photoluminescence ("PL") spectra were recorded using a Hitachi F-7000 FL spectrophotometer.

Figure 2A:
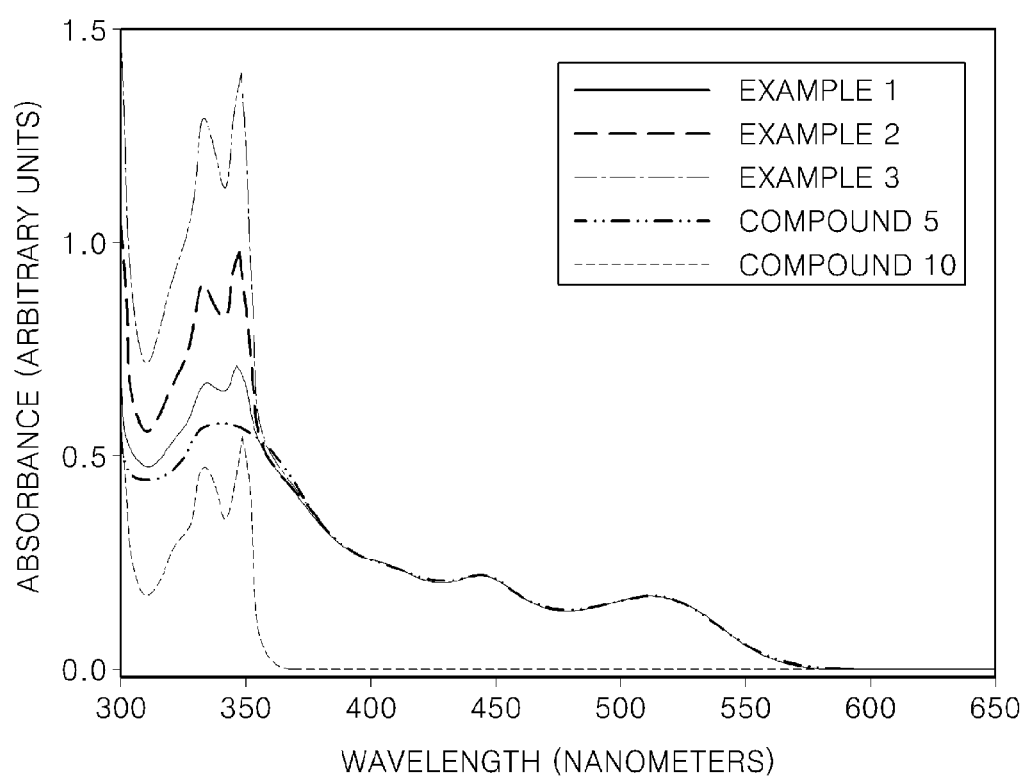
FIG. 2A shows UV-vis absorption spectra illustrating absorbance (arbitrary units) versus wavelength (nanometers, (nm)) of the phosphorescent dendrimers prepared according to Examples 1 to 3 and analyzed in solution according to Example 5.
Figure 2B:
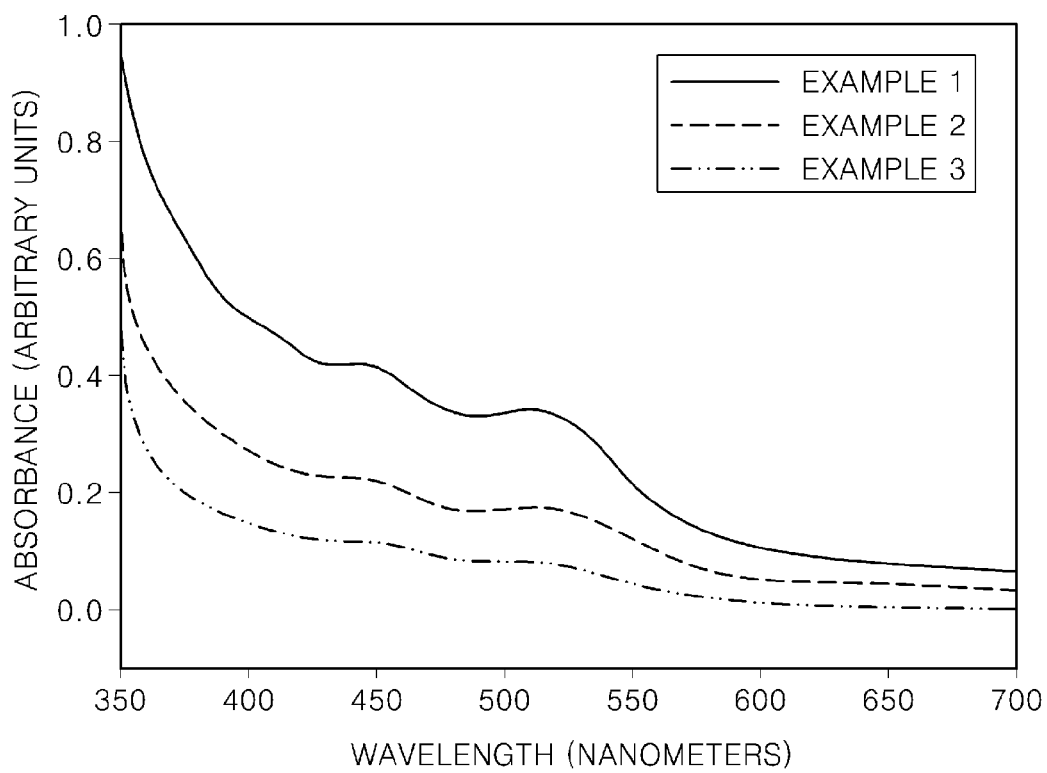
FIG. 2B shows UV-vis absorption spectra illustrating absorbance (arbitrary units) versus wavelength (nanometers, (nm)) of the phosphorescent dendrimers prepared in Examples 1 to 3 and analyzed as a film according to Example 5.

FIGS. 2A and 2B are UV-vis absorption spectra of the phosphorescent dendrimers prepared according to Examples 1 to 3. In chloroform, the absorption bands below 350 nm are ascribed to the π-π* transitions originating from the Ir complex and the carbazole. The intensity increases with the number of carbazole units. While not wanting to be bound by theory, it is understood that the increase in intensity with the number of carbazole units indicates that the amount of light absorbed by the carbazolyl dendritic antenna doubles with each generation. In a lower energy region from about 400 to about 570 nm, weak and broad absorption bands with shoulders (at about 443 and about 512 nm) may be observed, which may be attributed to the metal-to-ligand charge transfer ("MLCT") transitions of the Ir(III) complexes. It may be noticed that the spectra of the dendrimer is simply an addition of the spectra of Compound 5, which absorbs light at a wavelength of about 400 to about 570 nm, and Compound 10, which is based on carbazole using dendrons as a light-harvesting antenna. Also, the spectra do not show any other new interactive band between the carbazole and the Ir complex. Therefore, it is understood that the emission property of the Ir complex will not be affected due to non-conjugated tethering.

It is possible to obtain a strong emission from the central Ir(III) ion via sensitization from an excited carbazole-based light-harvesting antenna. Moreover, the site-isolation effect of the carbazole dendrons may also enhance luminance. When the solutions of dendrimers were excited at the absorption wavelength of the carbazole unit (e.g., $\lambda_{excitation}$=350 nm), they exhibited emission spectra with identical shape and a characteristic phosphorescent emission at about 641 to about 644 nm that is almost identical to that of the iridium (III) core used herein. This indicates that the dendritic structure did not affect the MLCT energy levels, which suggests emission from Ir(III) complexes with similar excited states and energies. It has already been confirmed that tethering the carbazole dendrons to the Ir(III) complex core unit via a non-conjugated alkylene spacer does not affect the optical properties significantly. Therefore, the Ir(III) complex unit was highly encapsulated by the multi-carbazole dendrons to isolate the photophysical properties.

Figure 3A:
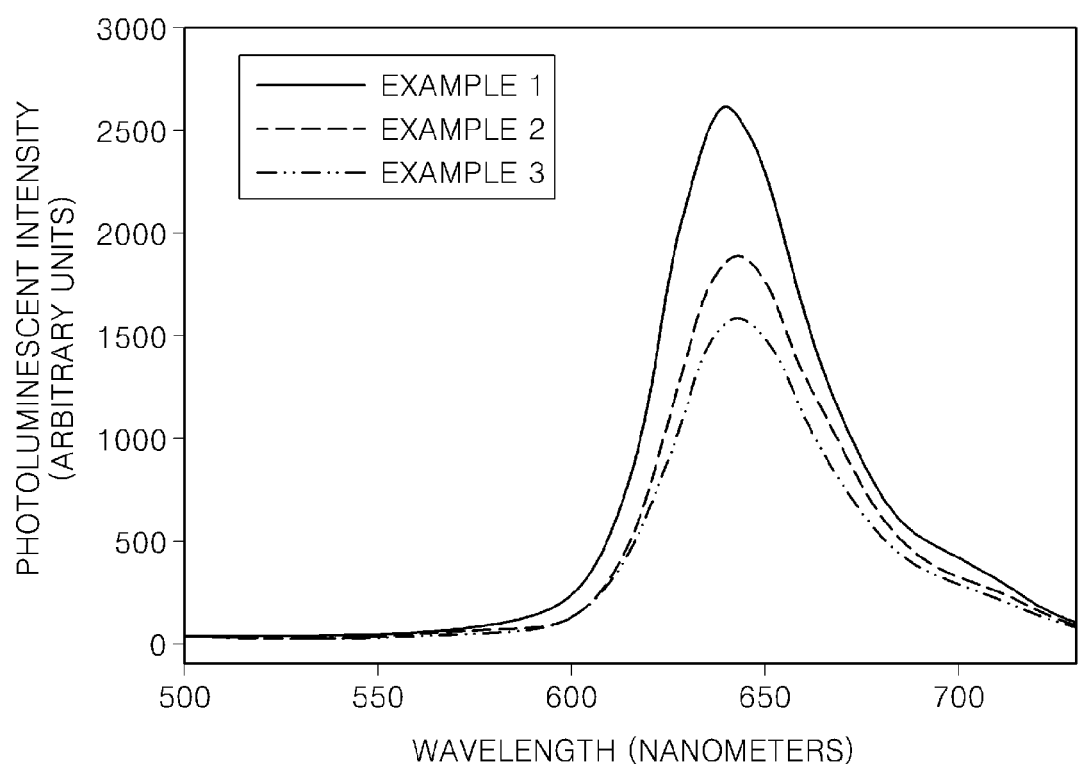
FIG. 3A shows photoluminescence spectra of the phosphorescent dendrimers prepared in Examples 1 to 3 and analyzed in a chloroform solution according to Example 5.
Figure 3B:
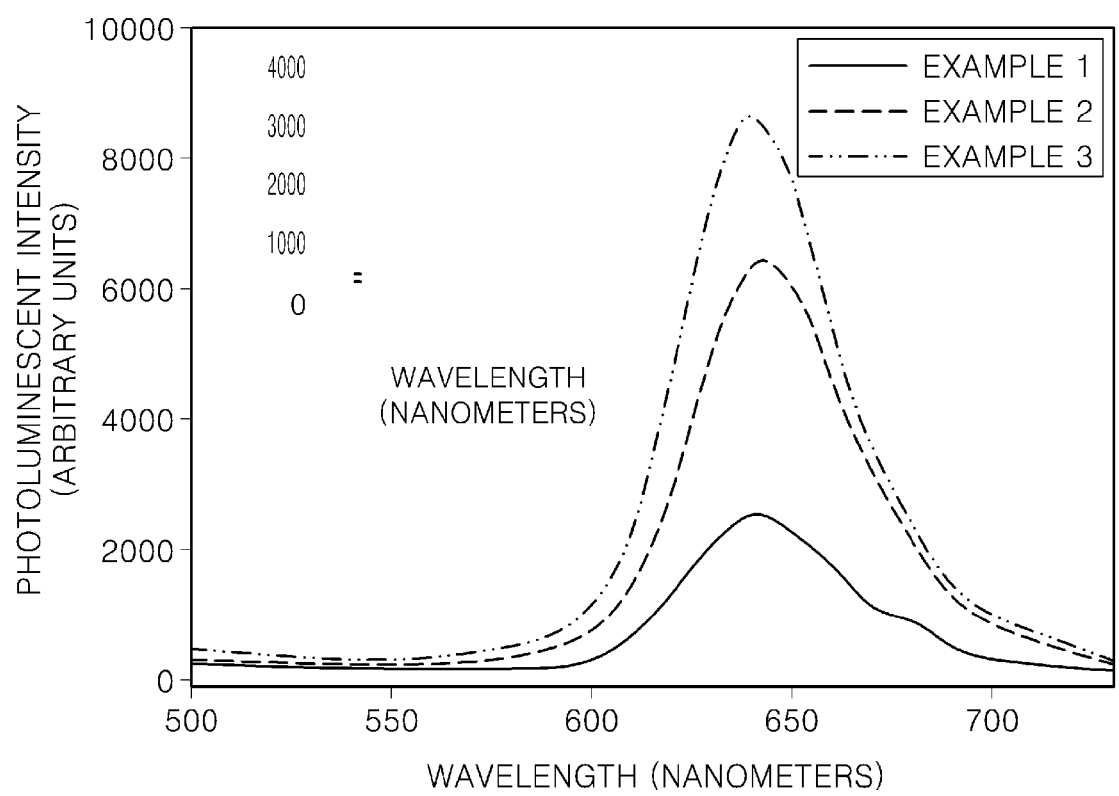
FIG. 3B shows photoluminescence spectra of the phosphorescent dendrimers prepared according to Examples 1 to 3 and analyzed as a film according to Example 5.
Figure 3C:
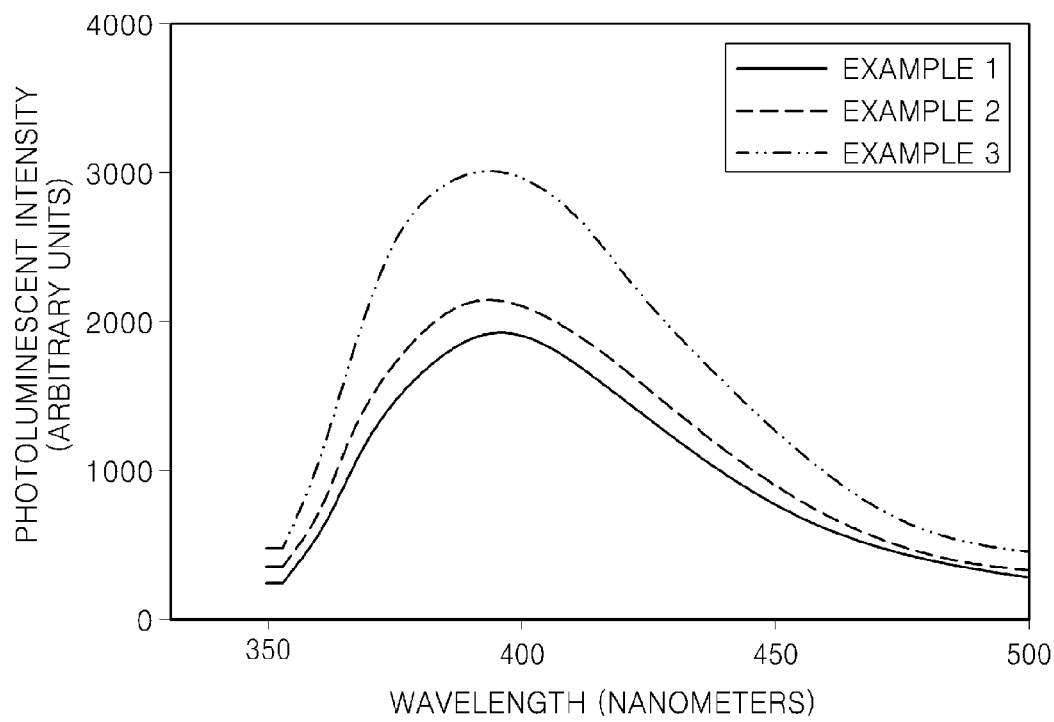
FIG. 3C shows residual emission spectra of the carbazolyl dendron in the phosphorescent dendrimers prepared in Examples 1 to 3 and analyzed as a film according to Example 5.

FIG. 3A shows a photoluminescence ("PL") spectra of the phosphorescent dendrimers prepared according to Examples 1 to 3 when analyzed as a chloroform solution. Referring to FIG. 3A, it may be noted that the emission intensity decreases with an increase in the number of generations. In the Examples, solutions having the same concentration of the phosphorescent dendrimer materials were prepared. With regard to the same concentration of the phosphorescent dendrimers, the lower generation phosphorescent dendrimer showed a higher mass percent of Ir complex as a central material. The higher generation of dendrimer showed lower concentration of emitting Ir complex, and thus emission intensity decreased. The same concentration of each dendrimer implies that the solution of the phosphorescent dendrimer of Example 3 contains less of the Ir(III) complex because of the higher density of the carbazole dendrons. FIG. 3B shows PL spectra of the phosphorescent dendrimers prepared according to Examples 1 to 3 when analyzed as a film and FIG. 2C shows residual emission spectra of the carbazolyl dendron in the phosphorescent dendrimers prepared in Examples 1 to 3 and analyzed as a film according to Example 5. The emission peak of the carbazolyl moiety in the film was partially quenched for all three dendrimers, indicating reasonably efficient energy transfer from the carbazole units to the Ir complex at the core as shown in FIG. 3C. Although the film thicknesses were almost identical, the largest dendrimer, which is the dendrimer of Example 3, exhibited the highest PL intensity, which may be due to reduced the inter-core interaction. This indicates that more efficient energy transfer between carbazole and the Ir(III) central core may occur without spatial geometrical congestion.

As illustrated in FIGS. 3A, 3B and 3C, the emission wavelength ("$\lambda_{em}$") of the solutions and films of the iridium phosphorescent dendrimers of Examples 1 to 3 were almost identical, indicating that the intermolecular interaction between the Ir(III) complexes was highly restricted.

As illustrated in FIG. 3A, the phosphorescent dendrimers of Examples 1 to 3 displayed simultaneous PL emission at about 641 to about 643 nm for the phosphorescent dendrimers of Examples 1 to 3, and the PL emission had the same shape in a solid state. This indicates that energy transfer does not occur between Ir complexes in the solid state. Thus, it may be seen that the Ir complex may be tethered so as to efficiently control a PL intensity. An identical number of dendrons was tethered to each ligand, resulting in the formation of a homoleptic phosphorescent dendrimer. Thus, while not wanting to be bound by theory, well-distributed carbazolyl dendrons enhance the site-isolation effect thereby avoiding undesirable photoluminescence.

Table 1 shows glass transition temperature ("$T_g$"), dissolution temperature ("$T_d$"), maximum absorption wavelength and the maximum wavelength of PL corresponding to the iridium phosphorescent dendrimers prepared in Examples 1 to 3.

TABLE 1

| | | Absorption | | Photoluminescence | |
|---|---|---|---|---|---|
| | | Solution | Film | Solution | Film |
| $T_g$ (° C.) | $T_d$ (° C.) | ($\lambda_{max}$/nm) | ($\lambda_{max}$/nm) | ($\lambda_{max}$/nm) | ($\lambda_{max}$/nm) |
| Example 1 | 105 | 360 | 444, 514 | 422, 510 | 641 | 644 |
| Example 2 | 78 | 365 | 444, 514 | 422, 510 | 643 | 643 |
| Example 3 | 72 | 370 | 444, 514 | 422, 510 | 644 | 641 |

Example 6

Preparation of Electroluminescence Devices

Figure 4A:
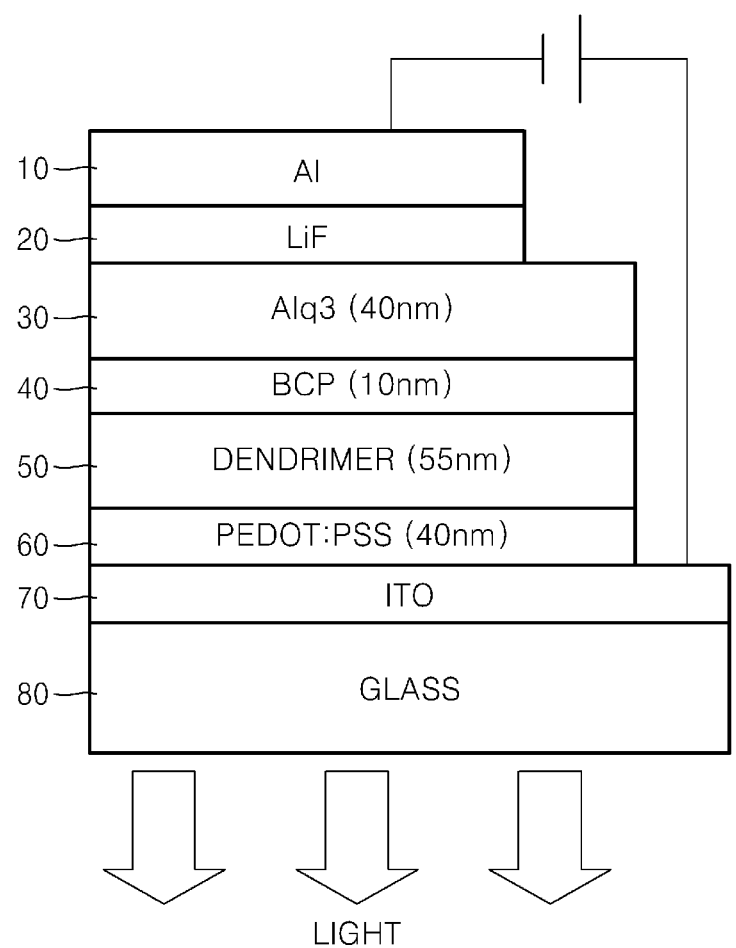
FIG. 4A is a schematic cross-section diagram of an exemplary embodiment of an electroluminescent device.

FIG. 4A shows an exemplary embodiment of an electroluminescent device. In an embodiment, the device comprises an Al layer 10 having a thickness of 100 nm on a LiF layer 20 having a thickness of 1 nm, which is on a tris-(8-hydroxyquinoline) aluminum ("$Alq_3$") layer 30 having a thickness of 40 nm, which is on a 2,9-dimethyl-4,7-diphenyl-1,10-phenanthroline ("BCP", i.e., bathocuprine) layer 40 having a thickness of 10 nm, which is on a dendrimer layer 50 having a thickness of 55 nm, which is on a poly(3,4-ethylenedioxythiophene) poly(styrenesulfonate) ("PEDOT:PSS") layer 60 having a thickness of 40 nm, which is on indium tin oxide 70, which is on glass 80. This structure may be expressed as ITO/PEDOT:PSS (40 nm)/dendrimer (55 nm)/BCP (10 nm)/$Alq_3$ (40 nm)/LiF (1 nm)/Al (100 nm). Referring to FIG. 4A, an electroluminescent device having the structure ITO/PEDOT:PSS (40 nm)/dendrimer (55 nm)/BCP (10 nm)/$Alq_3$ (40 nm)/LiF (1 nm)/Al (100 nm) was prepared. The conducting PEDOT:PSS layer was spin-coated onto the ITO-coated glass in an argon atmosphere. The emitting dendrimer layer was then spin-coated onto the thoroughly dried PEDOT layer using a solution having a concentration of 5 wt % in monochlorobenzene. Organic layers were grown by thermal evaporation at a base pressure of less than $5 \times 10^{-8}$ Torr in the following order: 10-nm-thick BCP as the hole-blocking layer ("HBL") and 40-nm-thick $Alq_3$ as the electron transport layer ("ETL"). Finally, LiF (1 nm)/Al (100 nm) electrodes were deposited onto the $Alq_3$ layer under the same conditions.

Current density-voltage-luminescence ("J-V-L") characteristics of the OLEDs were measured simultaneously using a Keithley 2400 programmable source meter and SpectraScan PR650 from Photo Research. The thickness of the dendrimer was determined using a TENCOR P-10 surface profilometer.

Table 2 shows turn-on voltage, maximum power efficiency, maximum luminous efficiency and maximum external quantum efficiency corresponding to electroluminescent devices prepared using the iridium phosphorescent dendrimers prepared according to Examples 1 to 3.

TABLE 2

| | Turn-On Voltage (V) | Maximum Luminance (cdm$^{-2}$)* | Maximum Power Efficiency (lmW$^{-1}$)* | Maximum Luminous Efficiency (cdA$^{-1}$)* | Maximum External Quantum Efficiency ($\eta_{ext}$)* |
|---|---|---|---|---|---|
| Example 1 | 5.0 | 561(383.427)** 12 V | 0.417(0.197)** 5 V | 0.664(0.197)** 5 V | 2.243(0.197)** 58 V |
| Example 2 | 5.5 | 1302(321.326)** 14 V | 0.953(0.169)** 5.5 V | 1.669(0.169)** 5.5 V | 5.552(0.169)** 5.5 V |
| Example 3 | 6.5 | 422(94.412)** 18 V | 0.819(0.412)** 7.5 V | 1.955(0.412)** 7.5 V | 6.115(0.412)** 7.5 V |

*Corresponding to J.
**the values in parentheses correspond to current density in mA/cm$^2$.

In table 2, V refers to Volts, cdm$^{-2}$ refers to candelas per square meter, lmW$^{-1}$ refers to lumens per watt, cdA$^{-1}$ refers to candela per ampere and $\eta_{ext}$ refers to external quantum efficiency.

Figure 4B:
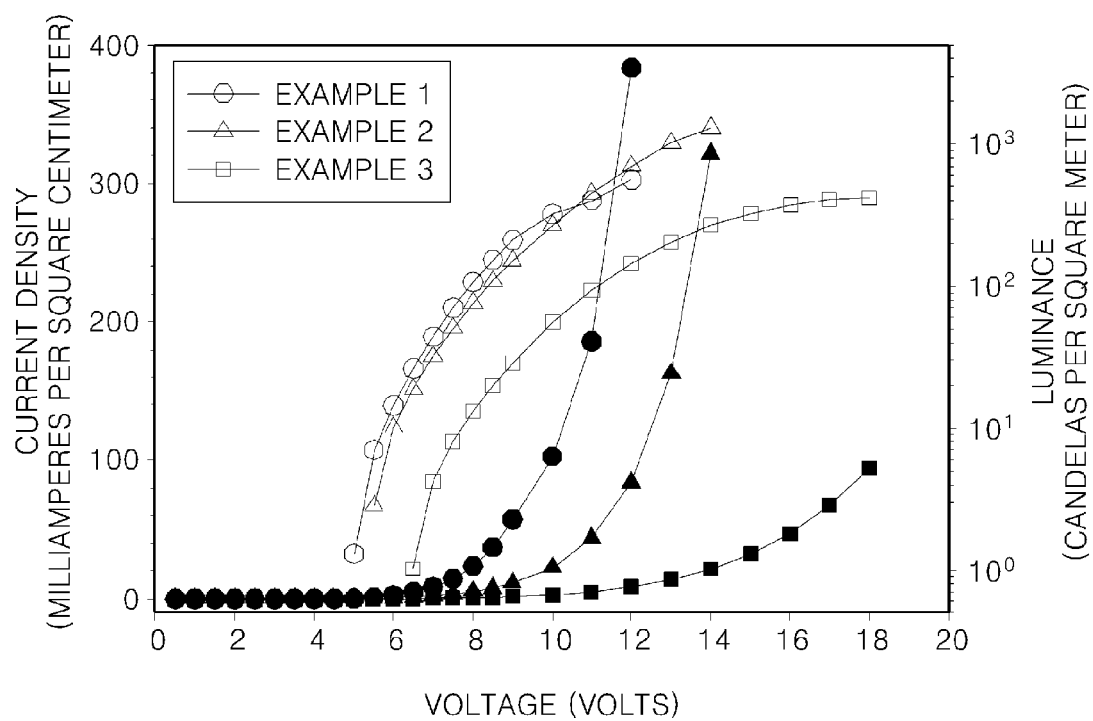
FIG. 4B is a graph illustrating current density (milliamperes per square centimeter ($mA/cm^2$)) and luminance (candelas ($cd/m^2$)) versus a voltage (volts (V)) of exemplary embodiments of electroluminescent devices containing the dendrimers of Examples 1 to 3, respectively.

FIG. 4B is a graph illustrating a current density and luminance versus voltage applied to the electroluminescent devices prepared according to Example 6. The turn-on voltages (e.g., electric field) of the electroluminescent devices were in the range of about 5.0 to about 6.5 V. The higher generation of dendrimer showed a slightly higher turn-on voltage, which is believed to be attributable to a higher dielectric constant corresponding to a greater content of the non-conjugated spacer and its moieties. The current density was highest for the electroluminescent device containing the dendrimer of Example 1 at a fixed bias voltage. While not wanting to be bound by theory, this result suggests that the mobility of the hole carrier is higher in the device containing the dendrimer of Example 1.

An electroluminescent device containing the photoluminescent dendrimer of Example 1 showed a lower efficiency than the electroluminescent device containing the dendrimer of Example 3, at a relatively low current density. The low external quantum efficiency may be attributed to the good hole-transporting properties but poor electron-transporting capabilities of the multi-layered device.

Figure 5A:
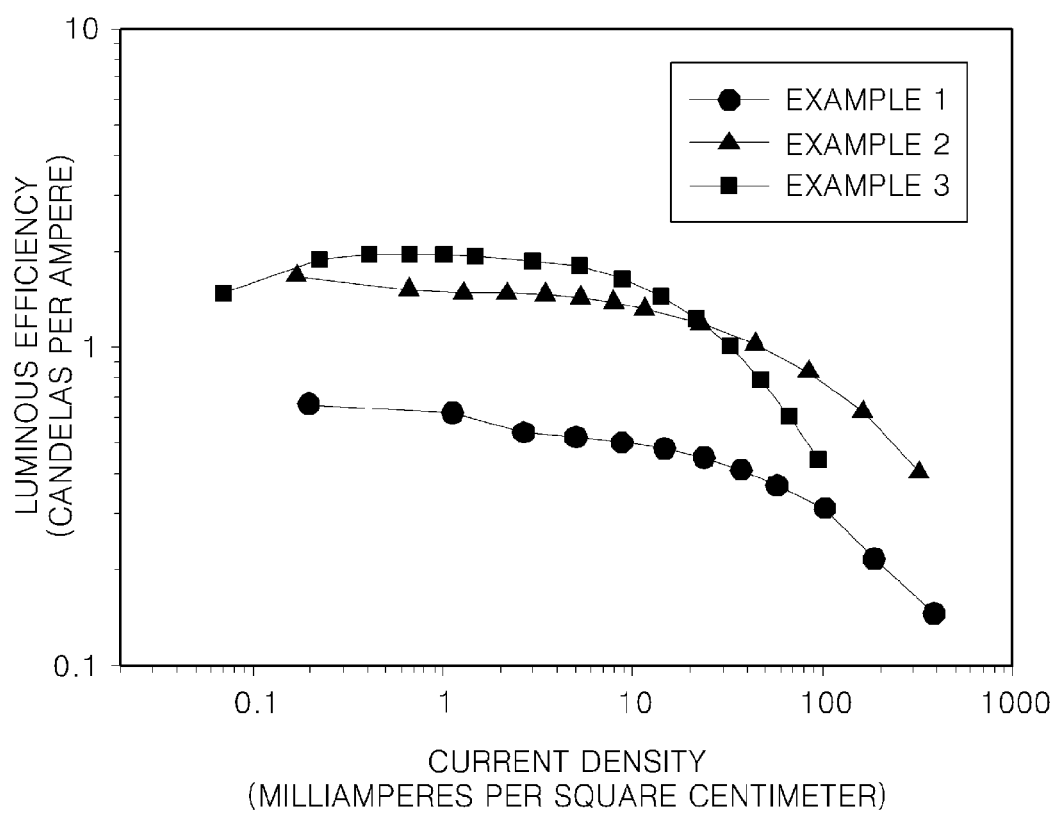
FIG. 5A is a graph of emission efficiency (candelas per ampere ($cdA^{-1}$)) versus current density ($mA/cm^2$) of exemplary embodiments of electroluminescent devices containing of the phosphorescent dendrimers of Examples 1 to 3, respectively.
Figure 5B:
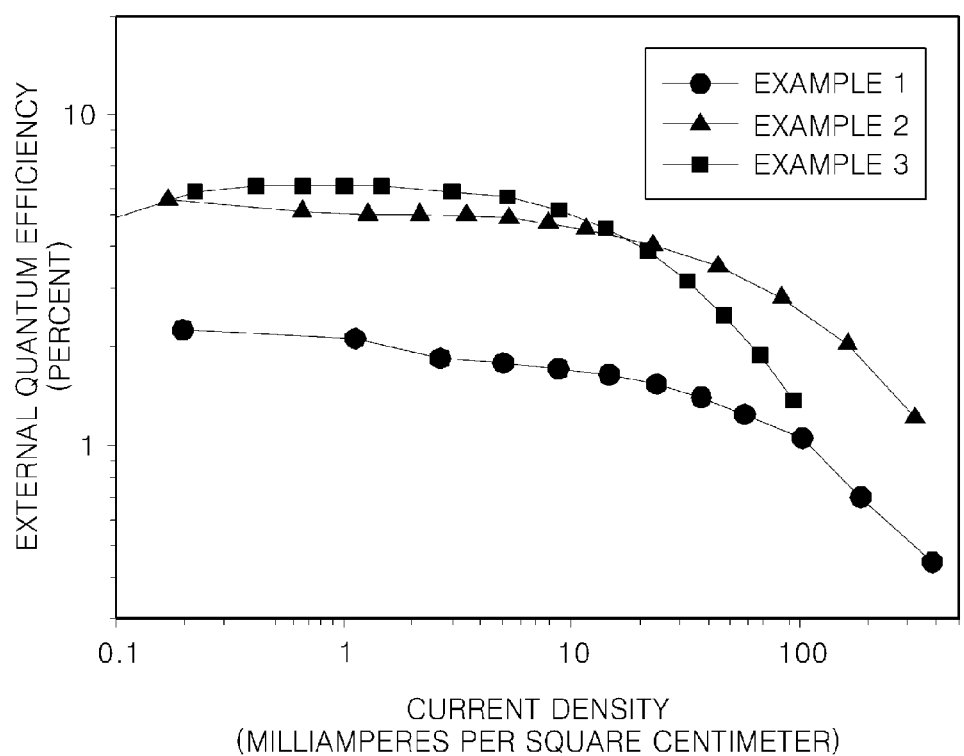
FIG. 5B is a graph of an external quantum efficiency ("EQE") (percent (%)) versus current density ($mA/cm^2$) of exemplary embodiments of electroluminescent devices containing the phosphorescent dendrimers of Examples 1 to 3, respectively.

With regard to the stability of efficiency, an electroluminescent device containing the dendrimer of Example 3 showed fast decay of both luminance efficiency and external quantum efficiency at a high current density, as illustrated in FIGS. 5A and 5B, respectively. It may be conjectured that hole and electron transport became unbalanced by acceleration of hole mobility rather than electron mobility.

Figure 6A:
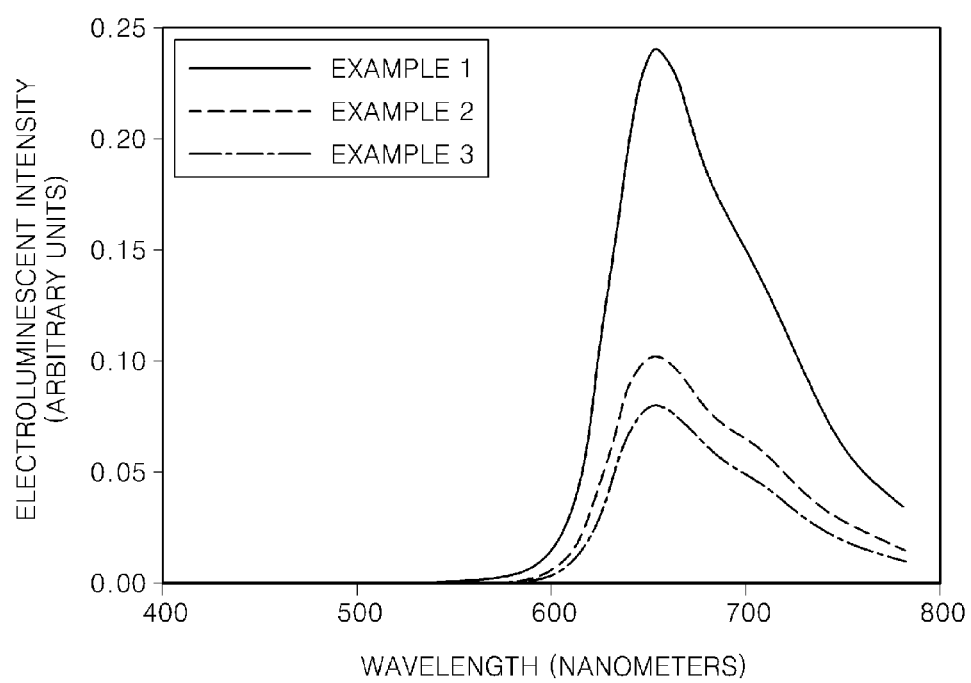
FIG. 6A shows electroluminescence ("EL") spectra illustrating electroluminescent intensity (arbitrary units) versus wavelength (nm) of an exemplary electroluminescent device containing the phosphorescent dendrimers of Examples 1 to 3, respectively, at maximum luminance.

FIG. 6A shows electroluminescence ("EL") spectra of the electroluminescent devices prepared according to Example 6, which contained the phosphorescent dendrimers of Examples 1 to 3, respectively, at maximum luminance. The phosphorescent dendrimers of Examples 1 to 3 exhibit deep-red emission, and the same excited state species is responsible for both PL and EL emission, except for some tail-like shoulder emission in the near-infra red ("NIR") region. No trace of emission from the tris-(8-hydroxyquinoline ("Alq$_3$") layer was observed in the EL spectra. At all forward bias voltages, only a characteristic red emission of the phosphorescent dendrimers of Examples 1 to 3, having a maximum EL emission at 652 to 656 nm, was observed. As the voltage increased, the emission mainly originated from the core emitting dye. The dendron density did not affect the EL spectra or the CIE coordinate even though the voltage applied to the sample was varied.

Figure 6B:
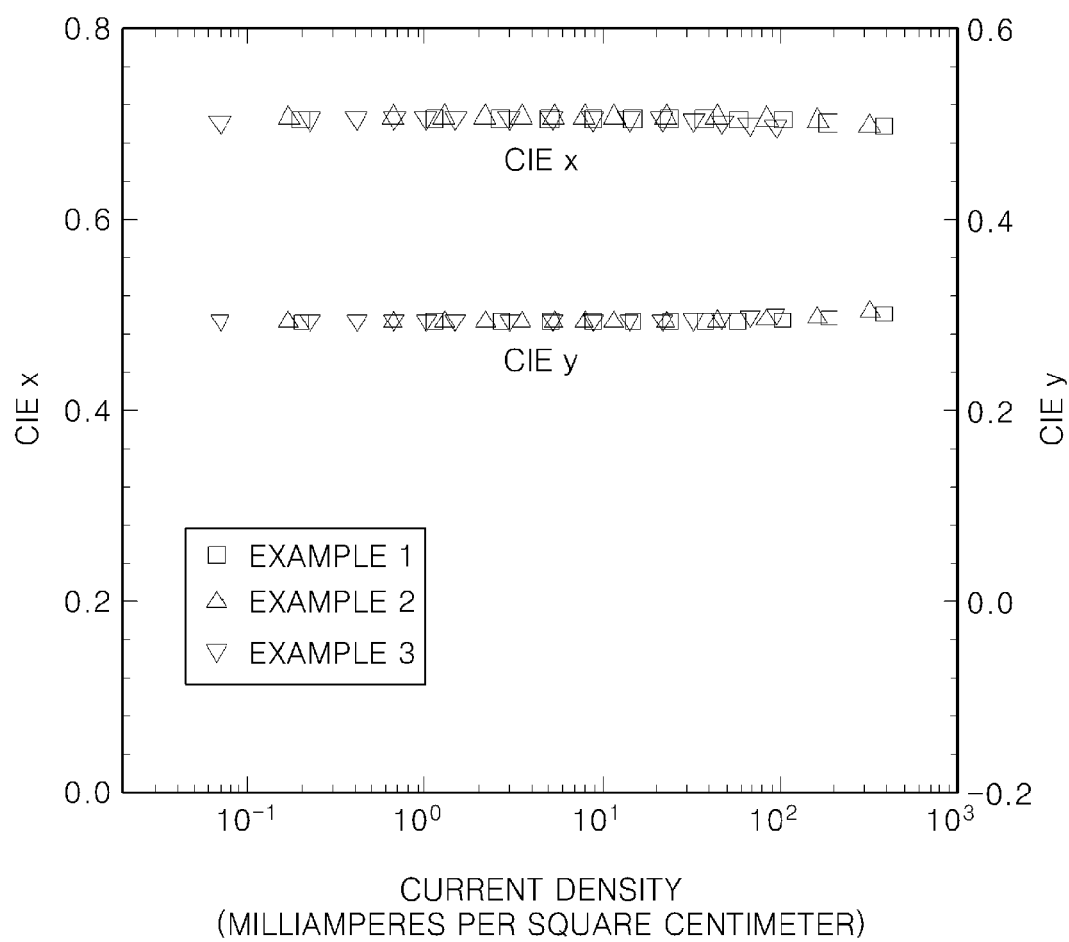
FIG. 6B is a graph illustrating chromaticity (i.e., CIE x and CIE y) versus current density ($mA/cm^2$) of exemplary embodiments of electroluminescent devices containing the phosphorescent dendrimer prepared according to Examples 1 to 3, respectively.

FIG. 6B is a graph illustrating chromaticity (i.e., CIE x and CIE y) versus current density of the electroluminescent devices containing the phosphorescent dendrimers of Examples 1 to 3. As is shown in FIG. 6B, to illustrate the stability of the electroluminescent devices, when the EL spectrum of the phosphorescent dendrimers was converted into chromaticity coordinates on the CIE 1931 diagram, a highly saturated deep red emission from three different generation dendrimers was obtained (x=0.70, y=0.30). This emission is close to the National Television System Committee (NTSC) standard for red color (x=0.67, y=0.33). The EL spectra of the phosphorescent dendrimers of Examples 1 to 3 were independent of the applied voltage when the voltage was varied from 6 V to 18 V. In addition, concomitant with an increase in the current density, the chromaticity remained stable with an increase in the applied voltage.

The disclosed phosphorescent dendrimer provides efficient energy transfer or exciton migration from the carbazole dendron to the Ir(III) acceptor moieties. That is, in the molecular architecture of the dendrimer with a carbazole dendron and a core unit, rapid energy transfer occurs from the light-harvesting dendron to the core unit. Thus, the molecular architecture of the dendrimer with a carbazole dendron and a core unit suppresses undesired short wavelength emission and leads to stabilized emission from these dendrimers due to rapid energy transfer from the light-harvesting dendron to the core unit. Also, the light emission of the electroluminescent devices fabricated with the dendrimers occurred solely from the components containing the low-bandgap structural materials, i.e., the Ir(III) red emitting core. Accordingly, an improved electroluminescent device may be prepared by using the disclosed phosphorescent dendrimers.

As described above, according to the one or more of the above embodiments, the iridium phosphorescent dendrimers exhibit good self-film forming properties, and thus the iridium phosphorescent dendrimers may be efficiently used in an electroluminescent device.

It should be understood that the exemplary embodiments described herein should be considered in a descriptive sense only and not for purposes of limitation. Descriptions of features, advantages or aspects within each embodiment should be considered as available for other similar features, advantages or aspects in other embodiments.

What is claimed is:

1. An iridium phosphorescent dendrimer represented by Formula 1:

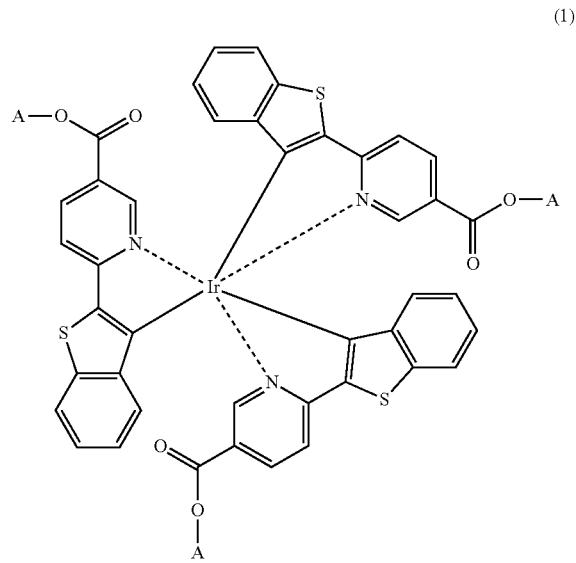

(1)

wherein A is a carbazole-based dendron.

2. The iridium phosphorescent dendrimer of claim 1, wherein A is represented by any one of Formulas 2, 3 and 4:

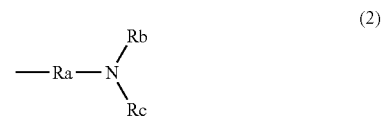

(2)

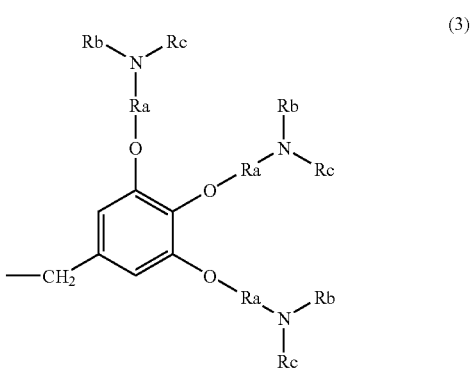

(3)

-continued

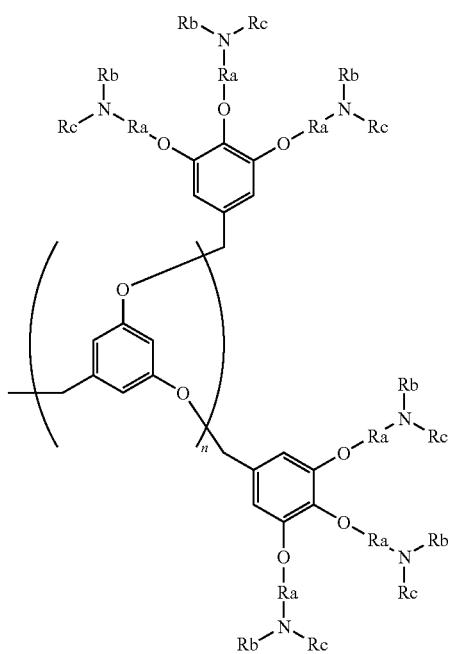

(4)

wherein

Ra is a $C_1$-$C_{22}$ alkylene group, a $C_2$-$C_{22}$ alkenylene group, a $C_5$-$C_{30}$ arylene group or a $C_6$-$C_{30}$ aminoarylene group, wherein the alkylene group, the arylene group or the aminoarylene group each optionally comprises at least one heteroatom selected from the group consisting of Si, B, O, P, N and S, Rb and Rc are each independently a $C_1$-$C_{22}$ alkylene group, a $C_5$-$C_{30}$ arylene group, or a $C_6$-$C_{30}$ aminoarylene group, wherein the alkylene group, the arylene group or the aminoaryl group each optionally comprises at least one heteroatom selected from the group consisting of Si, B, O, P, N and S, Rb and Rc are connected via a single bond, an alkylene group or an alkenylene group so as to form a fused ring, n is an integer from 1 through 5, and wherein the iridium phosphorescent dendrimer is homoleptic.

3. The iridium phosphorescent dendrimer of claim 1, wherein the iridium phosphorescent dendrimer is represented by any one of Formulas 6, 7 and 8:

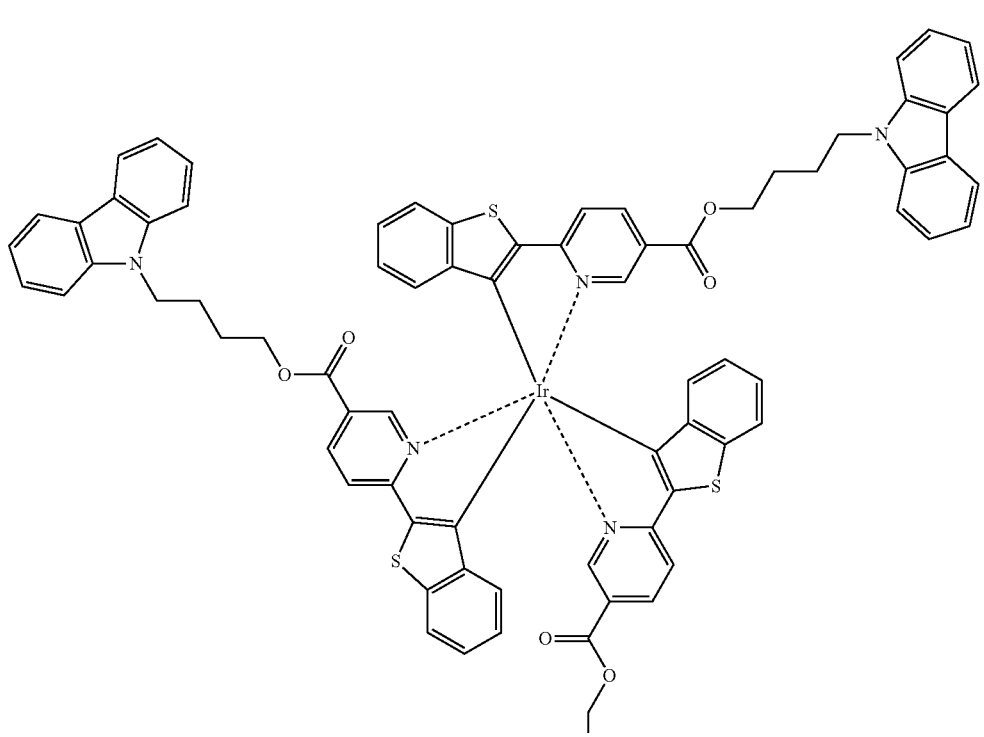

(6)

-continued
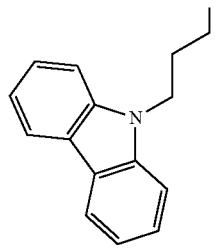
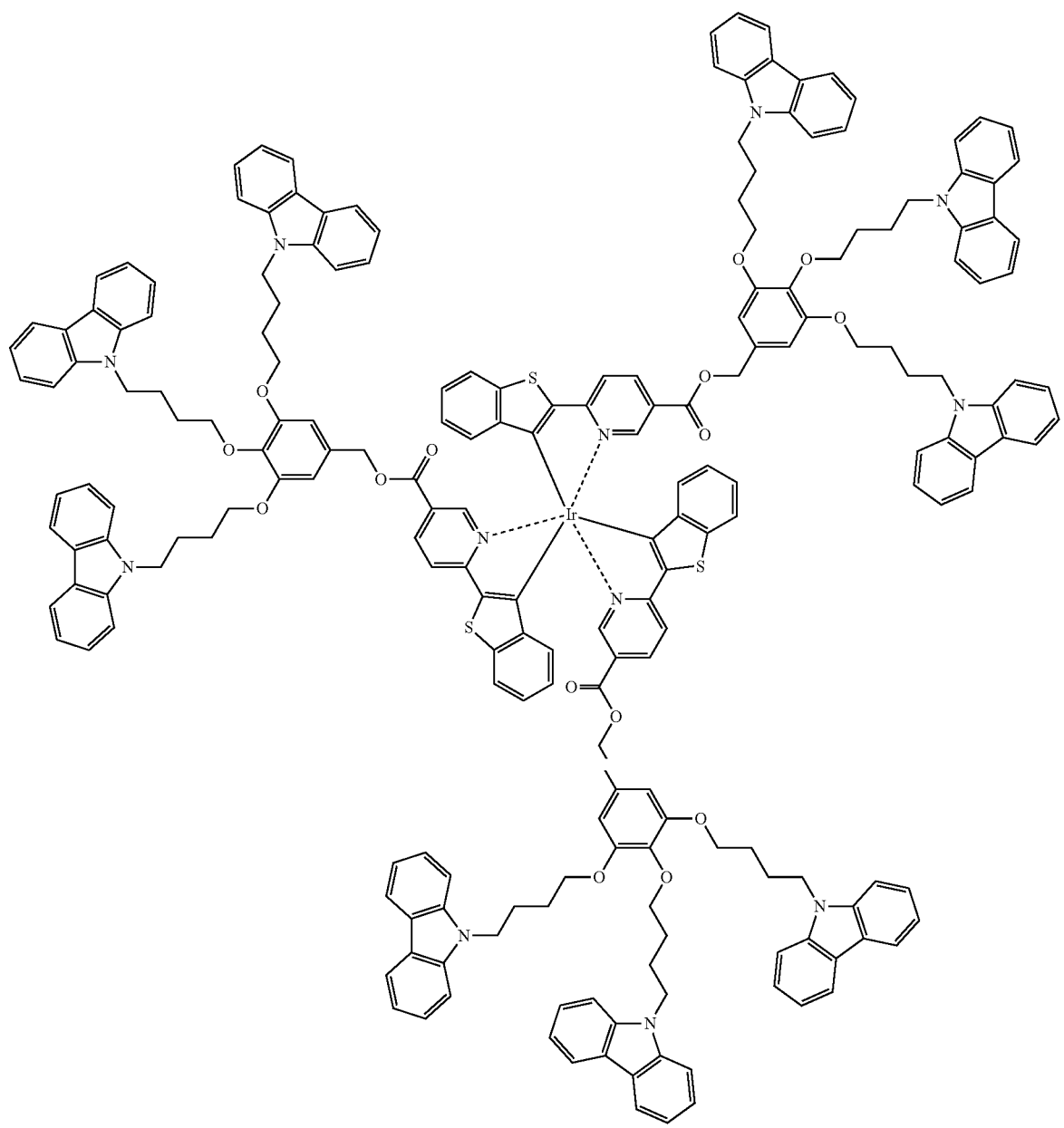
(7)

-continued
(8)
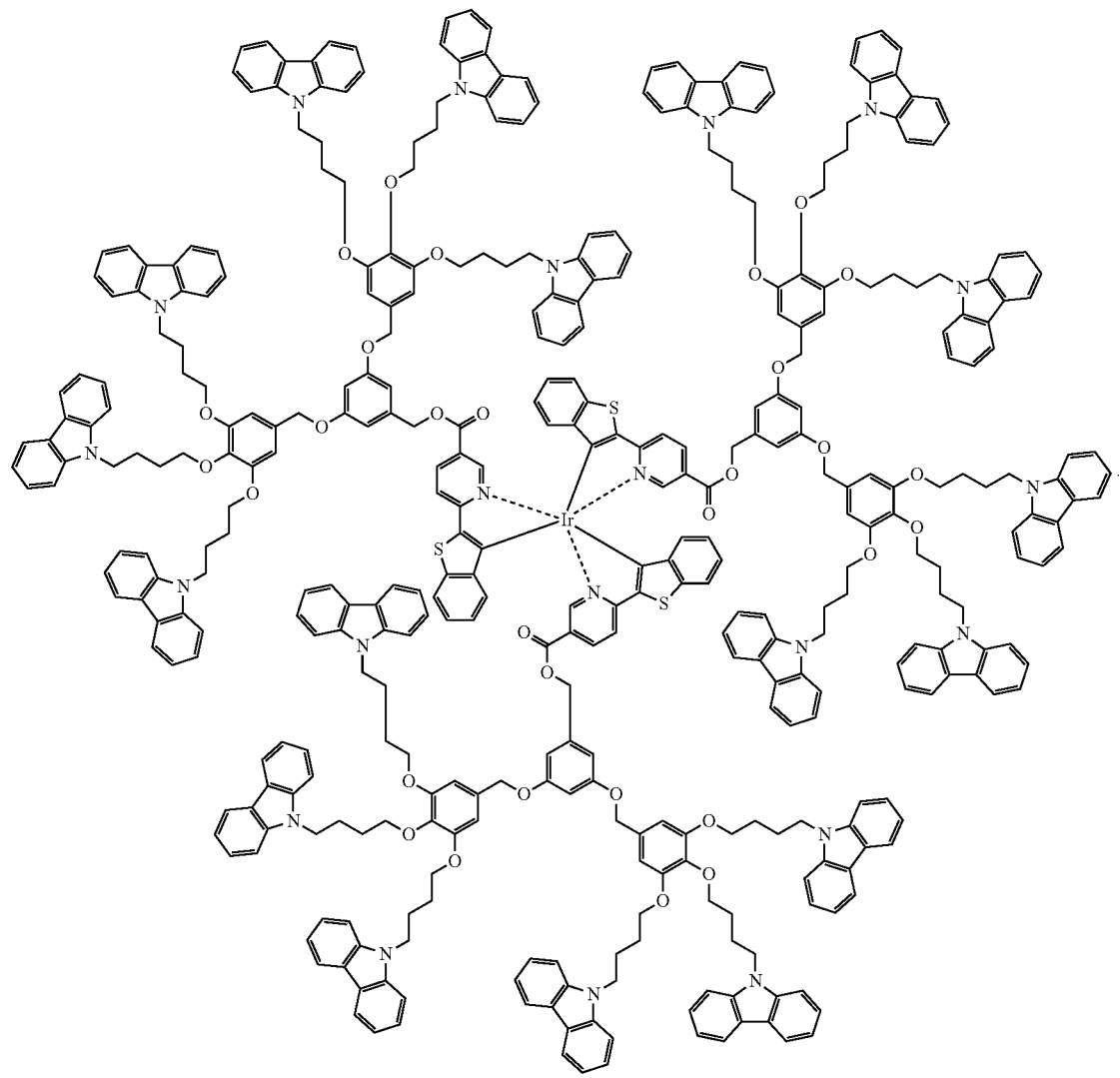
4. A method of preparing an iridium phosphorescent dendrimer represented Formula 1:
the method comprising:
contacting a tris-(2-benzo[b]thiophen-2-yl-nicotinic acid) Iridium (III) complex of Formula 5:
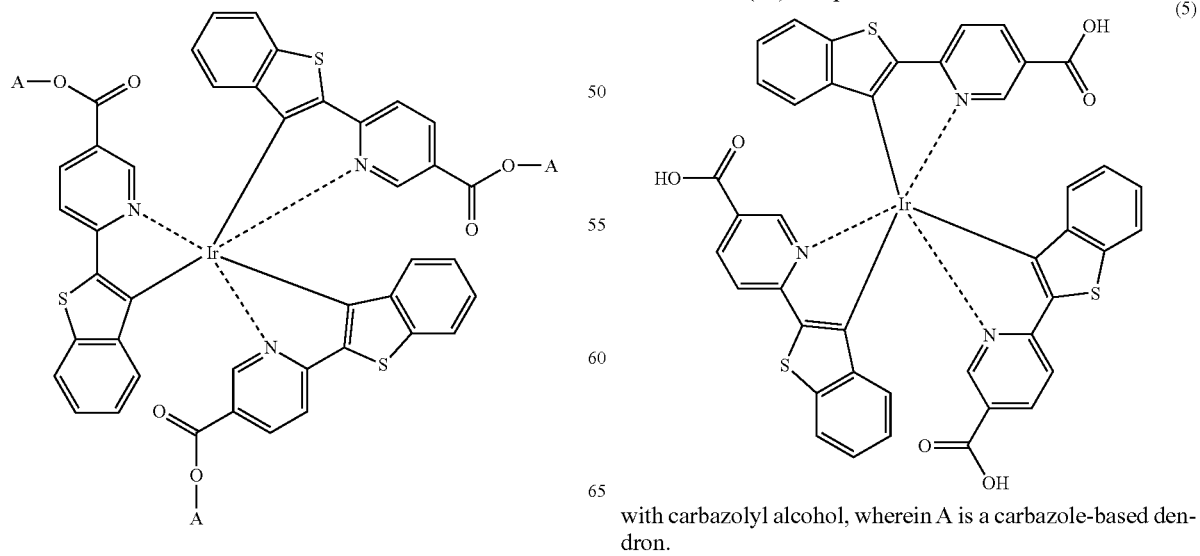
with carbazolyl alcohol, wherein A is a carbazole-based dendron.

5. The method of claim 4, where the tris-(2-benzo[b]thiophen-2-yl-nicotinic acid) Iridium (III) complex of Formula 5 is prepared by contacting a compound of Formula 9:

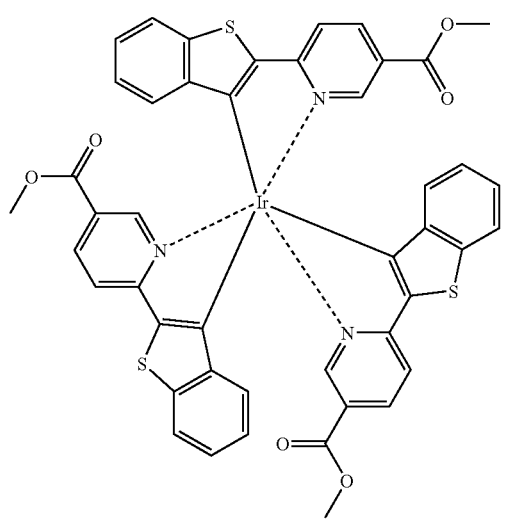

(9)

with lithium hydroxide monohydrate.

6. The method of claim 4, wherein the carbazolyl alcohol is represented by any one of Formulas 10, 11 and 12:

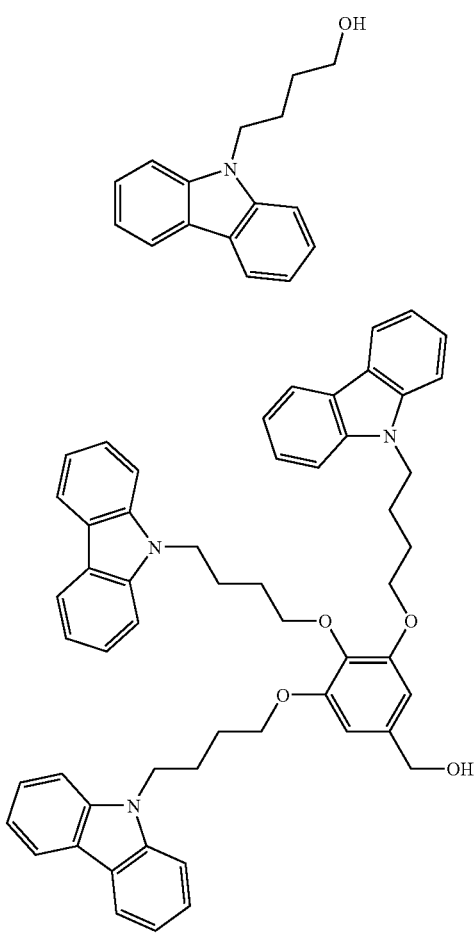

(10)

(11)

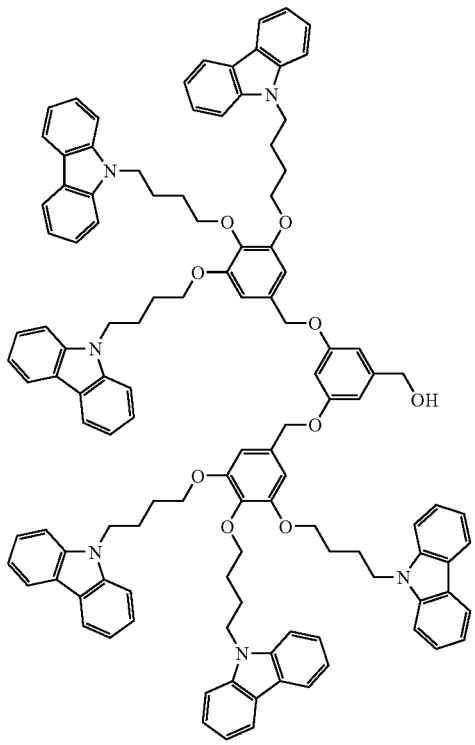

(12)

7. An electroluminescent device comprising:
an iridium phosphorescent dendrimer represented by Formula 1:

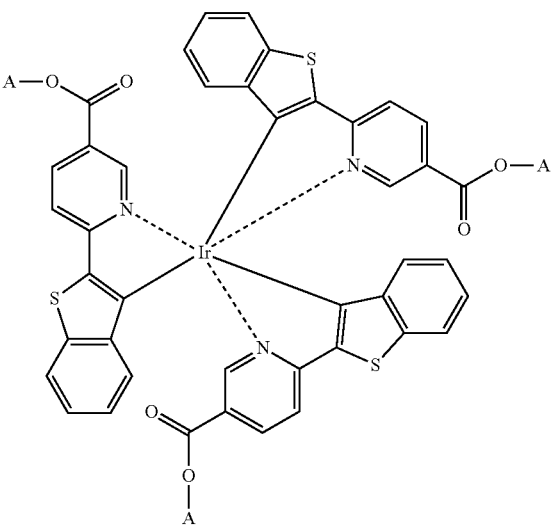

(1)

wherein A is a carbazole-based dendron.

8. The electroluminescent device of claim 7, wherein the iridium phosphorescent dendrimer emits red light.

9. The electroluminescence device of claim 7, wherein the electroluminescence device comprises a structure ITO/PEDOT:PSS (poly(3,4-ethylenedioxythiophene):poly(styrenesulfonate))/phosphorescent dendrimer/BCP(2,9-dimethyl-4,7-diphenyl-1,10-phenanthroline)/Alq$_3$(tris-(8-hydroxyquinoline) aluminum)/LiF/Al.

* * * * *